United States Patent [19]

Shimada et al.

[11] 4,167,506

[45] Sep. 11, 1979

[54] DIAZAPHENALENE DERIVATIVES AND RESIN CONTAINING COLOR COMPOSITIONS

[75] Inventors: Keizo Shimada, Hino; Toshiaki Harada; Masahiro Koga, both of Iwakuni; Shizuo Nagahama, Hino; Hiroyoshi Minematsu; Hidetsugu Yoshida, both of Iwakuni, all of Japan

[73] Assignee: Teijin Limited, Japan

[21] Appl. No.: 832,914

[22] Filed: Sep. 13, 1977

[30] Foreign Application Priority Data

Nov. 1, 1976 [JP] Japan .................................. 51-130426
Feb. 8, 1977 [JP] Japan .................................. 52-12046

[51] Int. Cl.$^2$ .......................................... C07D 471/06

[52] U.S. Cl. .............................. 260/37 N; 260/40 R; 260/42.14; 260/42.21; 260/42.45; 260/42.48; 106/288 Q; 8/1 D; 546/36; 546/51; 546/70; 544/125

[58] Field of Search ............ 260/287 P, 288 P, 289 C, 260/289 QP, 37 N; 106/288 Q; 8/1 D; 546/36; 544/125

[56] References Cited

FOREIGN PATENT DOCUMENTS 730692 5/1955 United Kingdom .

*Primary Examiner*—David E. Wheeler
*Attorney, Agent, or Firm*—Wenderoth, Lind & Ponack

[57] ABSTRACT

A group of novel polynuclear heterocyclic compounds having a diazaphenalene skeleton. These compounds assume orange to reddish violet colors according to the types of substituents on the diazaphenalene skeleton, and have excellent thermal stability and weatherability and good dispersibility in polymeric materials. They are useful as orange to reddish violet pigments, especially for coloring polymeric materials.

9 Claims, No Drawings

DIAZAPHENALENE DERIVATIVES AND RESIN CONTAINING COLOR COMPOSITIONS

This invention relates to novel polynuclear heterocyclic compounds. More specifically, it relates to a process for peparing novel diazaphenalene derivatives, and their use as orange to reddish violet pigments especially for coloring polymeric materials.

Polyazo, perylene and quinacridone pigments are among known orange to reddish violet pigments. These pigments, however, are not entirely satisfactory for industrial purposes because when used to color polymeric materials, they frequently have poor thermal stability and poor dispersibility in the polymeric materials, and shaped articles prepared from the polymeric materials having these pigments incorporated therein have poor dimensional stability.

It is an object of this invention to provide novel diazaphenalene derivatives which have superior thermal stability and weatherability and good dispersibillity especially in polymeric materials and can be extremely easily formed into pigments.

Another object of this invention is to provide a process for preparing these novel diazaphenalene derivatives at low cost.

Still another object of this invention is to provide orange to reddish violet pigments of high quality which have superior thermal stability and weatherability and good dispersibility especially in polymeric materials and do not adversely affect the properties of the polymeric materials.

A further object of this invention is to provide polymeric materials colored with these pigments.

Other objects and advantages of this invention will become apparent from the following detailed description.

The present invention provides a compound of the general formula

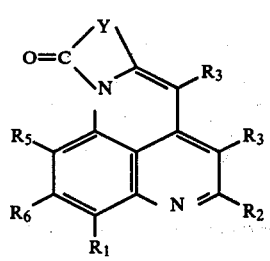

(I)

wherein
$R_1$ represents a hydrogen atom, a halogen atom, a hydroxyl group, a lower alkyl group, a lower alkoxy group, a lower haloalkyl group, an optionally substituted aryl group, a group of the formula

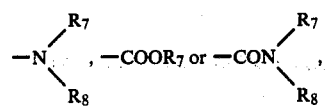

a group of the formula

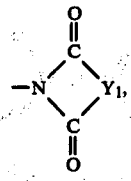

or a group of the formula

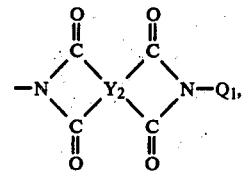

in which $R_7$ and $R_8$, independently from each other, represent a hydrogen atom, a lower alkyl group, an optionally substituted aryl group, an optionally substituted aralkyl group, an acyl group or a substituted 1,3,5-triazinyl group, or $R_7$ and $R_8$ together may form a heterocyclic ring together with the nitrogen atom to which they are bonded,
$Y_1$ represents a divalent aromatic group selected from groups of the formulae

with the two bonds being present ortho or peri to each other, and

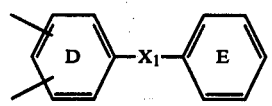

with the two bonds being present ortho to each other wherein ring A, ring B and/or C, and ring D and/or E each may have 1 to 10 substituents in total, $X_1$ represents a direct bond or —O—,

—$SO_2$—, —NHCO— or a lower alkylene group,
$Y_2$ reprsents a tetravalent aromatic group selected from groups of the formulae

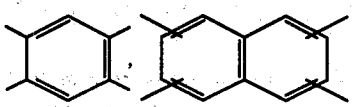

with the four bonds on the naphthalene ring forming two pairs and the two bonds in each pair being present ortho or peri to each other,

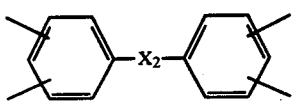

with the two bonds on each benzene ring being present ortho to each other, and

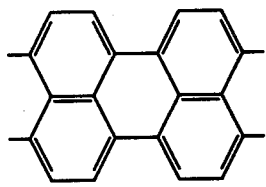

$Q_1$ is a monovalent group resulting from the removal of $R_1$ from formula (I) above, and $X_2$ represents

$-SO_2-$, $-CONH-$ or a lower alkylene group;

$R_2$; represents a hydrogen atom, a halogen atom, a lower alkyl group, a hydroxy group, a lower alkoxy group, a lower haloalkyl group, a group of the formula

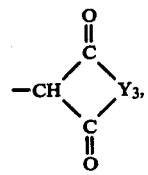

or a group of the formula

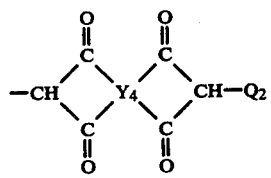

in which $Y_3$ is identical to or different from $Y_1$ and represents the same groups as done by $Y_1$, $Y_4$ is identical to or different from $Y_2$ and represents the same groups as done by $Y_2$, and $Q_2$ is a monovalent group resulting from the removal of $R_2$ from formula (I);

$R_3$, $R_5$ and $R_6$, independently from each other, represent a hydrogen atom, a halogen atom, a hydroxy group, a cyano group, a lower alkyl group, a lower alkoxy group, a lower haloalkyl group, or a group of the formula $-COOR_7$,

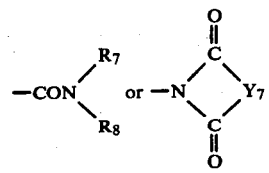

wherein $Y_7$ is identical to or different from $Y_1$ and represents the same groups as done by $Y_1$, and $R_7$ and $R_8$ are as defined above;

$R_4$ represents a hydrogen atom, a halogen atom, a lower alkyl group, a lower alkoxy group, a lower haloalkyl group, an optionally substituted aryl group, a cyano group, a group of the formula

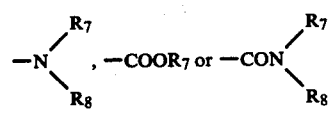

in which $R_7$ and $R_8$ are as defined above; and

Y represents a group of the formula $>Y_5$ in which $Y_5$ is identical from $Y_1$ and represents the same groups as done by $Y_1$, or a group of the formula $>Y_6=Q_3$ in which $Y_6$ is identical to or different from $Y_2$ and represents the same groups as done by $Y_2$, and $Q_3$ is a divalent group resulting from the removal of Y from formula (I).

When $R_2$ in formula (I) is a group of the formula

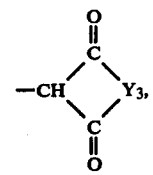

or a group of the formula

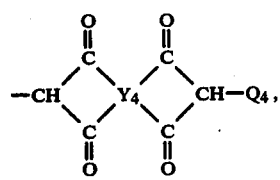

the compound of formula (I) can form tautomeric structures. When $R_2$ is

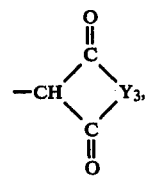

the tautomeric structures can be schematically shown as follows:

(I-2)

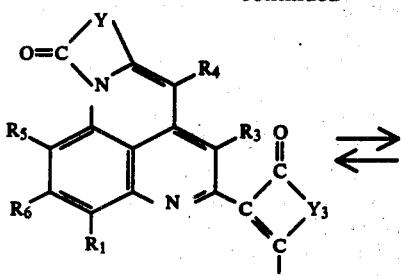

(I-1)

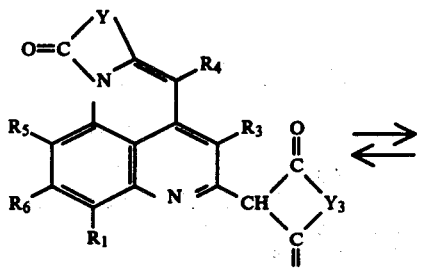

(I-3)

When R₂ is

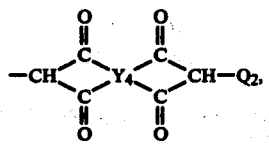

tautomeric structures corresponding to formula (I-2) and (I-3) can also be formed.

It is to be understood therefore that in the present specification and the appended claims, formula (I) is meant to include all of the tautomeric structures such as those expressed by formulae (I-2) and (I-3).

As a coloring ingredient of a pigment, the diazaphenalene derivative of formula (I) is used generally as a pigment preparation including various additives shown hereinbelow.

The pigment preparation can be formulated by usual methods. The additives used are, for example, dispersing agents, plasticizers, antioxidants, ultraviolet absorbers, antistatic agents, fire retardants, fillers, and reinforcing agents.

Examples of the dispersing agents include metal soaps such as zinc stearate, fatty acid-type compounds such as stearic acid, amides and esters thereof, and other various surface-active agents.

Examples of the plasticizers include phthalate esters such as di-(2-ethylhexyl phthalate), and phosphate esters such as tricresyl phosphate.

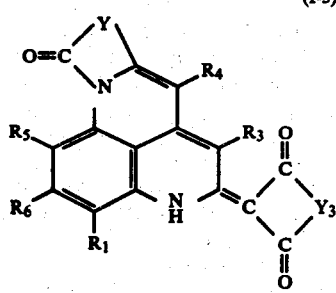

Examples of the antioxidants are hindered phenols such as 2,6-ditert-butyl-p-cresol.

Examples of the ultraviolet absorbers are phenyl salicylate compounds, benzophenone compounds, and benzotriazole compounds.

Examples of the antistatic agents are anionic surface-active agents such as guanidine compounds and sulfonic acid compounds, cationic surfce-active agents such as quaternary ammonium salts and imidazoline compounds; nonionic surface-active agents such as polyethylene glycol compounds and sorbitan compounds; and amphoteric surface-active agents such as betaine compounds.

Examples of the fire retardants are organic chlorine compounds, organic bromine compounds, antimony oxide-type fire retardants, and barium borate-type fire retardants.

The fillers are inorganic compounds such as kaolin, clay, and white carbon.

Examples of the reinforcing agents are inorganic a materials such as asbestos and glass fibers, synthetic fibers, and carbon fibers.

These additives are used in the amounts required according to particular purposes and known to those skilled in the art.

The proportion of the compound of formula (I) in the pigment preparation is at least 0.05% by weight, preferably 0.1 to 98% by weight, more preferably 1.0 to 90% by weight.

The pigment preparation can be used in various applications to be described hereinbelow.

In the present specification and the appended claims, the term "lower" used to define groups means that a group modified by this term contains up to 7 carbon atoms, preferably up to 5 carbon atoms, especially up to 3 carbon atoms.

In the present specification and the appended claims, the term "halogen atom" denotes fluorine, chlorine, bromine and iodine atoms, the first three being especially preferred. The "lower alkyl group" may be of straight chain or branched chain, and includes, for example, methyl, ethyl, n- or isopropyl, n- or iso-butyl, n- or iso-pentyl, and n-hexyl. Alkyl groups with up to 3 carbon atoms are suitable. The alkyl moiety in the "lower alkoxy group" may be of straight chain or branched chain. Examples of such lower alkoxy groups are methoxy, ethoxy, n- or iso-propoxy, n- or iso-butoxy, n-pentoxy, and n-hexyloxy. Alkoxy groups with up to 3 carbon atoms are suitable. The term "lower haloalkyl group" denotes a lower alkyl group substituted by at least one halogen atom, such as trifluoromethyl. The "lower alkylene group" may be of straight chain or branched chain, and includes, for example, methylene, ethylene, and n- or iso-propylene.

The term "aryl group" denotes a mononuclear or polynuclear aryl group containing up to 12 carbon atoms, preferably 6 to 10 carbon atoms, such as phenyl, naphthyl and biphenyl, the phenyl being especially suitable. The aryl group is optionally substituted. The substituent may be any of those substituents which are usually seen in the pigment chemistry. Specific examples of the substituents are alkyl groups such as methyl or ethyl, alkoxy groups such as methoxy or ethoxy, alkylamino groups, arylamino groups, an amide group, substituted amide groups, acyl groups, and an amino group. The aryl group may also be substituted by an aromatic imide group of the formula

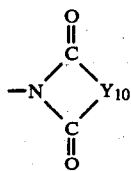 (VI)

wherein $Y_{10}$ is identical to or different from $Y_1$, and represents the same groups as done by $Y_1$, which is formed by reacting an amino group (—$NH_2$) that may be present on the aryl group, with a carboxylic anhydride or its reactive derivatice to be described below.

Thus, preferred substituents on the aryl group are lower alkyl, lower alkoxy, amide, and imide groups. Of these, the aromatic imide groups of formula (VI) are suitable. The term "optionally substituted aralkyl group" denotes a lower alkyl group substituted by an optionally substituted aryl group, and the aryl moiety and the lower alkyl moiety of the aralkyl group have the meanings given hereinabove. Examples of suitable substituted aralkyl groups are benzyl and phenethyl groups.

The term "acyl group" means an atomic group resulting from the removal of OH from the carboxyl group of a carboxylic acid, and generaly those represented by the formula $R_9$—CO— are conveniently used. In the formula, $R_9$ is a monovalent hydrocarbon group suitably containing up to 10 carbon atoms, preferably lower alkyl groups, or a phenyl group. Examples of suitable acyl groups are acetyl, propionyl and benzyl.

The 1,3,5-triazinyl group represented by $R_7$ or $R_8$ in formula (I) is expressed by the following formula

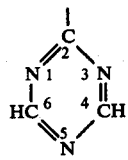

and the carbon atoms at the 4- and 6-positions of this group are distributed by the same or different groups. Examples of the substituents are optionally substituted arylamino groups such as phenylamino, chlorophenylamino, and N-methylphenylamino; optionally substituted alkylmino groups such as 1-methyl(4-N,N-diethylamino)-butylamino; and groups of the formula —NH—$Q_1$ in which $Q_1$ is as defined hereinabove. Of these, chloropheylamino, N-methylphenylamino, and the groups —NH—$Q_1$ are preferred.

The heterocyclic ring formed by $R_7$ and $R_8$ in conjunction with the nitrogen atom to which they are bonded is suitably 5- or 6-membered. The heterocyclic ring may contain at least one, preferably only one, hetero atom such as oxygen, sulfur or nitrogen in addition to the nitrogen atom which originally constitutes the heterocyclic ring. Examples of the heterocyclic ring are pyrrolidine, piperidine, and morpholine.

Examples of suitable amino, ester or carbamoyl groups of the formula

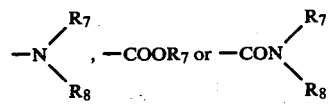

include —$NH_2$, —$NHCOCH_3$, —$NHCH_3$, —$COOCH_3$, —$CONH_2$, and $CON(CH_3)_2$.

The benzene ring or naphthalene ring A, B, C, D or E in the divalent atomatic group represented by $Y_1$ in formula (I) is unsubstituted, or may contain up to 10, preferably up to 6, more preferably up to 4, substituents in total. The substituents may be any groups known in the field of the pigment chemistry. Specific examples of such substituents include halogen atoms; a carboxyl group; ester groups of the formula —$COOR_{10}$ in which $R_{10}$ has the same meaning as group $R_7$ defined hereinabove, especially lower alkoxycarbonyl groups such as methoxycarbonyl, ethoxycarbonyl or propoxycarbonyl; optionally substituted arylsulfonyl groups, especially optionally substituted benzenezulfonyl groups such as benzenesulfonyl, p-chlorobenzesulfonyl, o-chlorobenzenesulfonyl, o-methyl-benzenesulfonyl, and o-methoxybenzenesulfonyl; and dicarboxylic acid anhydride groups

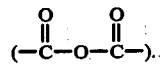

Of these, halogen atoms, carboxyl groups, lower alkoxycarbonyl groups, optionally substituted benzenesulfonyl groups and dicarboxylic anhydride groups are preferred.

Specific examples of the divalent aromatic group represented by $Y_1$ are as follows:

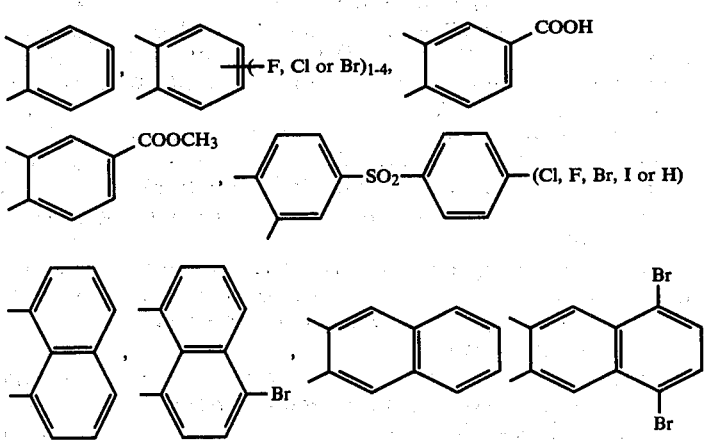

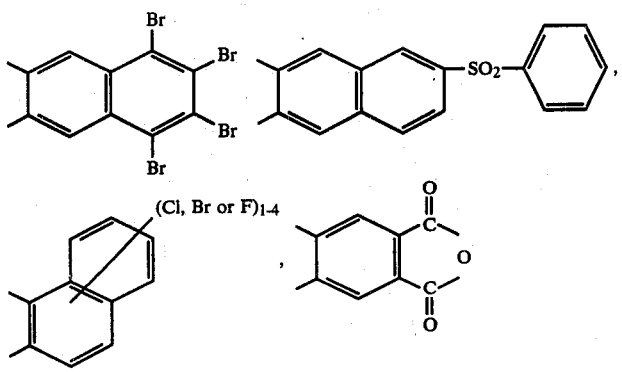

Specific examples of the tetravalent aromatic group represented by $Y_2$ in formula (I) are given below.

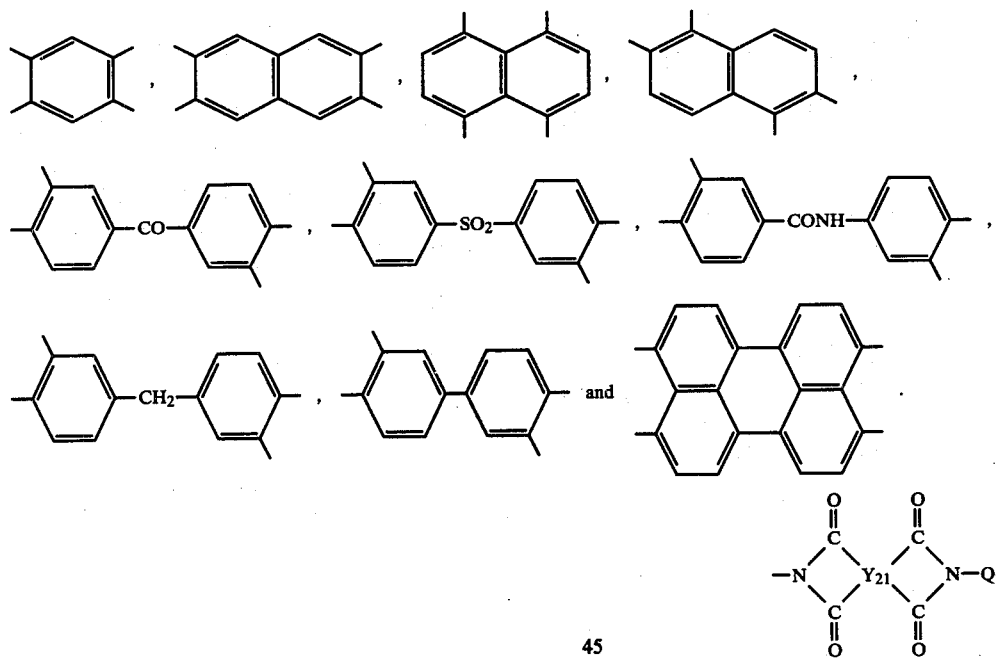

Thus, in the compounds of formula (I) provided by this invention, preferred atoms or atomic groupings represented by $R_1$ are a hydrogen atom, halogen atoms, a hydroxyl group, lower alkyl groups, lower alkoxy groups, optionally substituted phenyl groups, groups of the formula

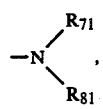

—COOR$_{71}$ or —CONHR$_{71}$, groups of the formula

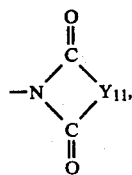

and groups of the formula

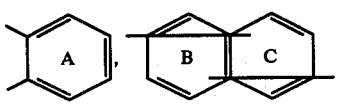

in which $R_{71}$ and $R_{81}$, independently from each other, represent a hydrogen atom, a lower alkyl group, an optionally substituted phenyl group, an optionally substituted phenyl-lower alkyl group, an acyl group or a substituted 1,3,5-triazinyl group, $Y_{11}$ represents a divalent aromatic group selected from the group consisting of groups of the formulae

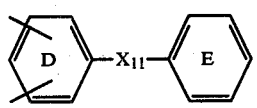

with the two bonds being present ortho or peri to each other, and with the two bonds being present ortho to each other wherein ring A, ring B and/or C, and ring D and/or E may contain up to 6 substituent in total selected from halogen atoms, a carboxyl group, lower alkoxycarbonyl groups, optionally substituted arylsulfonyl groups and dicarboxylic acid anhydride groups, $X_{11}$ represents

or $-SO_2-$, $Y_{21}$ represents a group of the formula

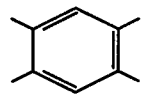

a group of the formula

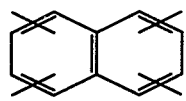

with the four bonds on the naphthalene ring forming two pairs, and the two bonds in each pair being present ortho or peri to each other, or a group of the formula

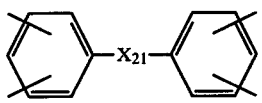

with the two bonds on each benzene ring being present ortho to each other, $Q_{11}$ is a monovalent group resulting from the removal of group $R_1$ from formula (I), and $X_{21}$ represents

or $-SO_2-$.

Preferred species of group $R_2$ include a hydrogen atom, lower alkyl groups, groups of the formula

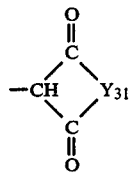

or groups of the formula

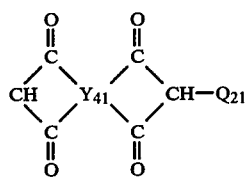

in which $Y_{31}$ is identical to or different from $Y_{11}$ and represents the same groups as done by $Y_{11}$, $Y_{41}$ is identical to or different from $Y_{21}$, and represents the same groups as done by $Y_{21}$, and $Q_{21}$ is a monovalent group resulting from the removal of group $R_2$ from formula (I).

Preferred species of $R_3$, $R_5$ and $R_6$, independently from each other, are a hydrogen atom, halogen atoms, a hydroxy group, lower alkyl groups, lower alkoxy groups, and groups of the formula $-NHR_{71}$, $-COOR_{71}$, or $-CONHR_{71}$, in which $R_{71}$ is as defined hereinabove.

Advantageously, $R_4$ is a hydrogen atom, a lower alkyl group, or an optionally substituted phenyl group.

Preferred species of Y are groups $Y_{51}$ in which $Y_{51}$ is identical to or different from $Y_{11}$ and represents the same groups as done by $Y_{11}$, the groups $-Y_{61}=Q_{31}$ wherein $Y_{61}$ is identical to or different from $Y_{21}$ and represents the same groups as done by $Y_{21}$ and $Q_{31}$ is a divalent group resulting from the removal of Y from formula (I).

Thus, especially preferred species of the compounds of formula (I) provided by this invention are those of the formula

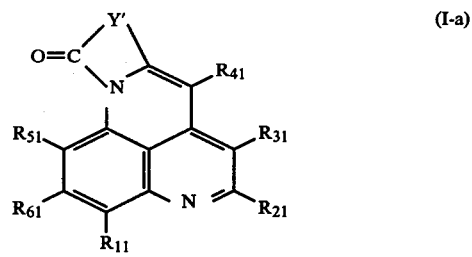

(I-a)

wherein $R_{11}$ represents a hydrogen atom, a halogen atom, a hydroxyl group, a lower alkyl group, a lower alkoxy group, or a phenyl group optionally substituted by a group of the formula

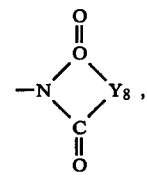

a group of the formula

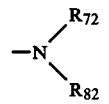

a group of the formula

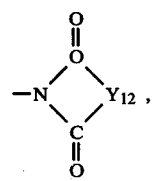

or a group of the formula

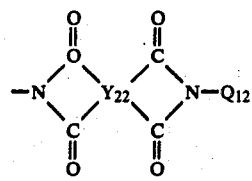

in which $R_{72}$ and $R_{82}$, independently from each other, represent a hydrogen atom, a lower alkyl group, a phenyl group, a benzyl group, an acyl group derived from a carboxylic acid, or a 1,3,5-triazinyl group which is di-substitued by a group selected from the class consisting of optionally substituted phenylamino groups and groups of the formula —NH—$Q_{12}$, $Y_{12}$ represents a divalent aromatic group selected from the class consisting of

with the two bonds being present ortho or peri to each other and

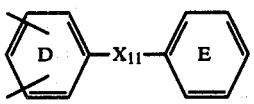

with the two bonds being present ortho to each other wherein ring A, ring B and/or C, and ring D and/or E may contain up to 6, especially up to 4, substituents selected from the group consisting of halogen atoms, a carboxyl group, lower alkoxycarbonyl groups, optionally substituted benzenesulfonyl groups and dicarboxylic acid anhydride groups, $X_{11}$ represents

or —$SO_2$—, $Y_{22}$ represents a tetravalent aromatic group selected from the class consisting of

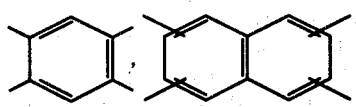

with the four bonds on the naphthalene ring forming two pairs and the two bonds in each pair being present ortho or peri to each other, and

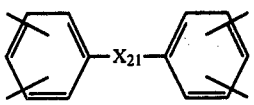

with the two bonds on each benzene ring being present ortho to each other, $Y_8$ is identical to or different from $Y_{12}$, and represents the same groups as done by $Y_{12}$, $Q_{12}$ is a monovalent group resulting from the removal of $R_{11}$ from formula (I-a), and $X_{21}$ represents

or —$SO_2$—;
$R_{21}$ represents a hydrogen atom, a lower alkyl group, a group of the formula

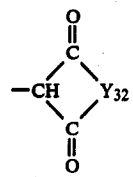

or a group of the formula

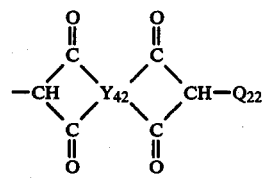

in which $Y_{32}$ is identical to or different from $Y_{12}$ and represents the same groups as done by $Y_{12}$, $Y_{42}$ is identical to or different from $Y_{22}$ and represents the same groups as done by $Y_{22}$, and $Q_{22}$ is a group resulting from the removal of group $R_{21}$ from formula (I-a);
$R_{31}$, $R_{51}$ and $R_{61}$, independently from each other, represent a hydrogen atom, a halogen atom, a hydroxy group, a lower alkyl group or a lower alkoxy group;
$R_{41}$ represents a hydrogen atom, a lower alkyl group, or a phenyl group optionally substituted by

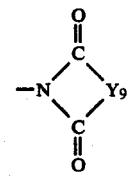

in which $Y_9$ is identical to or different from $Y_{12}$ and represents the same groups as done by $Y_{12}$; and
Y' represents the group $Y_{52}$ which is identical to or different from $Y_{11}$ and represents the same groups as done by $Y_{11}$, or a group of the formula =$Y_{62}$=$Q_{32}$ in which $Y_{62}$ is identical to or different from $Y_{22}$ and represents the same groups as done by $Y_{22}$, and $Q_{32}$ is a divalent group resulting from the removal of Y' from formula (I-a).

Typical examples of the novel diazahenalene derivatives of formula (I) or (I-a) provided by this invention, except those specifically shown in Examples to ge given hereinbelow, are as follows:
(1) Indeno-[2,1-a]-4,12a-diazaphenalen-12-one;
(2) 7-Methyl-8,9,10,11tetrachloro-indeno[2,1-a]-4,12a-diazaphenalen-12-one;
(3) 3-Chloroindeno-[2,1-a]-4,12a-diazaphenalen-12-one;

(4) 7-Methyl-3,8,9,10,11-pentachloro(or pentabromo)-indeno-[2,1-a]-4,12a-diazaphenalen-12-one;

(5) 3-Benzoylamino-indeno-[2,1-a]-4,12a-diazaphenalen-12-one;

(6) 3-[tetrachlorophthalimido]-7-methyl-8,9,10,11-tetra-chloroindeno-[2,1-a]-4,12a-diazaphenalen-12-one;

(7) 5-Methyl-[9,10-benzo]-indeno-[2,1-a]-4,12a-diazaphenalen-12-one;

(8) 5-Ethyl-7-methyl-8,9,10,11-tetrachloro(or tetrabromo)-indeno-[2,1-a]-4,12a-diazaphenalen-12-one;

(9) 3,5-Dimethylindeno-[2,1-a]-4,12a-diazaphenlen-12-one;

(10) 3,5,6,7-Tetramethylindeno-[2,1a-diazaphenalen-12one;

(11) 5-Methyl-3,8,9,10,11-pentachloro(or pentabromo)-indeno-[2,1-a]-4,12a-diazaphenalen-12-one;

(12) 3-Chloro-5,7-dimethyl-8,9,10,11-tetrabromo-indeno-[2,1-a]-4,12a-diazaphenalen-2-one;

(13) 3[1,8-Naphthalimido]-5-metylindeno-[2,1-a]-4,12a-diazaphenalen-12-one;

(14) 3-[Tetrachlorophthalimido]-5,7-dimethyl-8,9,10,11-tetrachloroindeno-[2,1-a]-4,12a-diazaphenalen-12-one;

(15) 2,4,14-Trimethyldibenzo-[ef, no]-3,6b-diazanaphthacen-7-one;

(16) 3-Ethyl-7-methyl-5-[2-inden-1,3(2H)-dinoyl]-indeno-[2,1-a]-4,12a-diazaphenalen-12-one;

(17) 3-Methyl-5-[4,5,6,7-tetrachloro-2-inden-1,3(2H)-dionyl]-indeno-[2,1-a]-4,12a-diazaphenalen-12-one;

(18) 3-Ethyl-7-methyl-5-[4,5,6,7-tetrachloro-2-inden-1,3(2H)-dionyl]-8,9,10,11-tetrachloro(or tetrabromo)-indeno-[2,1-a]-4,12a-diazaphenalen-12-one;

(19) 3,6-Dimethyl-5-[4,5,6,7-tetrachloro-2-inden-1,3(2H)-dionyl]-indeno-[2,1-a]-4,12a-diazaphenalen-12-one;

(20) 3-Chloro-7-methyl-5-[4,5,6,7-tetrachloro-2-inden-1,3(2H)-dionyl]-indeno-[2,1-a]-4,12a-diazaphenalen-12-one;

(21) 3-Ethyl-5-[2-inden-1,3(2H)-dionyl]-indeno-[2,1-a]-4,12a-diazaphenalen-12-one;

(22) 3,8,9,10,11-Pentachloro-5-[4,5,6,7-tetrachloro-2-inden-1,3(2H)-dionyl]-7-methyl-indeno-[2,1-a]-4,12a-diazaphenalen-12-one;

(23) 3-Bromo-8,9,10,11-tetrachloro-5-[4,5,6,7-tetrabromo-2-inden-1,3(2H)-dionyl]-indeno-[2,1-a]-4,12a-diazaphenalen-12-one;

(24) 3,8,9,10,11-Pentachloro-5-[5,6-benzo-2-inden-1,3(2H)-dionyl]-7-methyl-indeno-[2,1-a]-4,12a-diazaphenalen-12-one;

(25) 3-Chloro-9,12-dibromo-5-[4,5-6,7-tetrachloro-2-inden-1,3(2H)-dionyl]-benzo-[5,6]-indeno-[2,1-a]-4,14a-diazaphenalen-14-one;

(26) 3-Chloro-9,10,11,12-tetrabromo-7-methyl-5-[5,6,7,8-tetrabromo-benzo-[5,6]-2-inden-1,3(2H)-dionyl]-benzo-[5,6]-indeno-[2,1-a]-4,14a-diazaphenalen-14-one;

(27) 3,8,9,10,11-Pentachloro-5-[benzo-[4,5]-inden-1,3(2H)-dionyl]-indeno-[2,1-a]-4,12a-diazaphenalen-12-one;

(28) 3,6,7-Trimethyl-5-[4,5,6,7-tetrachloro-2-inden-1,3(2H)-dionyl]-benzo-[5,6]-indeno-[2,1-a]-4,14a-diazaphenalen-14-one;

(29) 3-Ethyl-6-methyl-5-[4,5,6,7-tetrachloro-2-inden-1,3(2H)-dionyl]-indeno-[2,1-a]-4,12a-diazaphenalen12-one;

(30) 3-(Tetrachlorophthalimido)-5-[4,5,6,7-tetrachloro-2-inden-1,3(2H)-dionyl]-7-methyl-8,9,10,11-tetrachloroindeno-[2,1-a]-4,12a-diazaphenalen-12-one;

(31) 3-Benzoylamino-5-[4,5,6,7-tetrachloro-2-inden-1,3(2H)-dionyl]-8,9,10,11-tetrachloroindeno-[2,1-a]-4,12a-diazaphenalen-12-one;

(32) 3-[4-Bromo-1,8-naphthalimido]-5-[4,5,6,7-tetrachloro-2-inden-1,3(2H)-dionyl]-7-methyl-8,9,10,11-tetrachloroindeno-[2,1-a]-4,12a-diazaphenalen-12-one;

(33) 3-Methyl-5-[2-phenalen-1,3-(2H)-dionyl]-8,9,10,11-tetrachloroindeno-[2,1-a-diazaphenalen-12-one;

(34) 2-[4,5,6,7-tetrachloro-2-inden-1,3(2H)-dionyl]-4-chloro-14-methyl-dibenzo-[ef, no]-3,6b-diazanaphthacen-7-one;

(35) 3,7-Dimethyl-5-[4,5,6,7-tetrachloro-2-inden-1,3(2H)-dionyl]-8,9,10,11-tetrachloroindeno-[2,1-a]-4,12a-diiazaphenalen-12-one;

(36) 3-Chloro-5-[2-inden-1,3(2H)-dionyl]-7-[p-phthalimidophenyl]-indeno-[2,1-a]-4,12a-diazaphenalen-12-one;

(37) 3-Methyl(or Chloro)-5-[5-carboxy-2-inden-1,3(2H)-dionyl]-8,9,10,11-tetrachloroindeno-[2,1-a]-4,12a-diazaphenalen-12-one;

(38) 3-Chloro-5-[4,5,6,7-tetrachloro-2-inden-1,3(2H)-dionyl]-9(or 10)-carboxy-indeno-[2,1-a]-4,12a-diazaphenalen-12-one;

(39) 2,6-bis[3-methyl-indeno-[2,1-a]-4,12a-diazaphenalen-12-on-5-yl]-5-indacene-1,3,5,7-(2H, 6H)-tetraone;

(40) 2,7-bis[3-bromo-9(or 10)-carboxy-indeno-[2,1-a]-4,12a-diazaphenalen-12-on-5-yl]-pyrene-1,3,6,8-(2H, 7H)-tetraone;

(41) 3-Chloro-9(or 10)-nitro-5-[4,5,6,7-tetrachloro-2-inden-1,3(2H)-dionyl]-indeno-[2,1-a]-4,12a-diazaphenalen-12-one;

(42) 7-Cyano-5-[4,5,6,7-tetrachloro-2-inden-1,3(3(2H)-dionyl]-ideno-[2,1-a]-4,12a-diazaphenalen-12-one;

(43) 3-Methyl-7-phenyl-5-[4,5,6,7-tetrachloro-2-inden-1,3(2H)-dionyl]-8,9,10,11-tetrachloro-indeno-[2,1-a]-4,12a-diazaphenalen-12-one;

(44) 1-Chloro-3-methoxy-5-[4,5,6,7-tetrachloro-2-inden-1,3(2H)-dionyl]-indeno-[2,1-a]-4,12a-diazaphenalen-12-one;

(45) 3-methoxycarbonyl-5-[inden-1,3(2H)-dionyl]-indeno-[2,1-a]-4,12a-diazahenalen-12-one;

(46) 3-fluoromethyl-5-[inden-1,3(2H)-dionyl]-indeno-[2,1-a]-4,12a-diazaphenalen-12-one;

(47) 3-Anilinocarbonyl-5-[2-inden-1,3(2H)-dionyl]-indeno-[2,1-a]-4,12a-diazaphenalen-12-one;

(48) 3-(p-naphthoylphenyl)-5-[2-inden-1,3(2H)-dionyl]-indeno-[2,1-a]-4,12a-diazaphenalen-12-one;

(49) 3-Hydroxy-5-[4,5,6,7-tetrachloro-2-inden-1,3(2H)-dionyl]-indeno-[2,1-a]-4,12a-diazaphenalen-12-one;

(50) 3-Dimethylamino-5-[2-inden-1,3(2H)-dionyl]-indeno-[2,1-a]-4,12a-diazaphenalen-12-one;

(51) N,N'-[3-(8,9,10,11-tetrachloro-indeno-[2,1-a]-4,12a-diazaphenalen-12-onyl)]-pyromellitic diimide;

(52) N,N'-[3-indeno-[2,1-a]-4,12a-diazaphenalen-12-onyl)]-diphenylether-3,4,3',4'-tetracarboxylic diimide;

(53) N,N'-[3-(indeno-[2,1-a]-4,12a-diazaphenalen-12-onyl)]-naphthalene-1,4,5,8-tetracarboxylic diimide;

(54) 1-Methoxy-5-[4,5,6,7-tetrachloro-2-inden-1,3(2H)-dionyl]-indeno-[2,1-a]-4,12a-diazaphenalen-12-one.

The novel diazaphenalene derivative of formula (I) can be prepared in accordance with this invention by (a) reacting a compound of the general formula

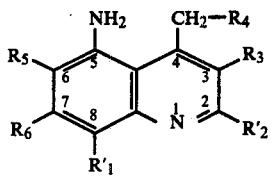

(II)

wherein $R'_1$ is identical to or different from $R_1$ and represents the same groups as done by $R_1$; $R'_2$ is identical to or different from $R_2$ and represents the same groups as done by $R_2$; and $R_3$, $R_4$, $R_5$ and $R_6$ are as defined hereinabove, with a carboxylic anhydride of the general formula

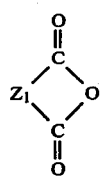

(III-1)

wherein $Z_1$ represents a group $>Y_5$ as hereinabove defined, a group of the formula

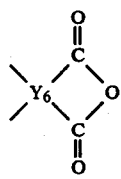

or a group of the formula $>Y_6=Q_3$, and $Y_5$, $Y_6$ and $Q_3$ are as defined hereinabove, or its reactive derivative;

(b) heating a compound of the general formula

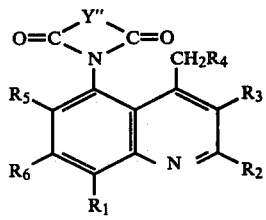

(IV-1)

wherein $Y''$ represents the same groups as done by $Y$, or represents a group of the formula $>Y_6=Q_4$ in which $Y_6$ is as defined above and $Q_4$ represents a divalent group resulting from the removal of $Y''$ from formula (IV-1); and $R_1$, $R_2$, $R_3$, $R_4$, $R_5$ and $R_6$ are as defined hereinabove, or (c) reacting a compound of the general formula

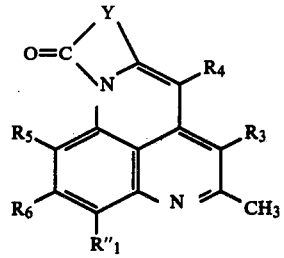

(I-b)

wherein $R''_1$ is identical to or different from $R_1$ and represents the same groups as done by $R_1$, and $R_3$, $R_4$, $R_5$, $R_6$ and $Y$ are as defined hereinabove, with a carboxylic anhydride of the formula

(III-2)

wherein $Z_2$ represents the group $Y_3$, a group of the formula

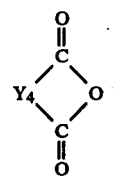

or a group of the formula

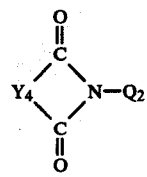

and $Y_3$, $Y_4$ and $Q_2$ are as defined hereinabove, or its reactive derivative; or (d) reacting a compound of the general formula

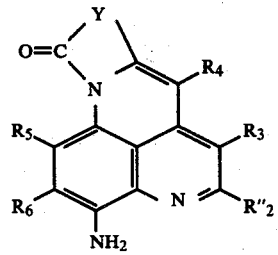

(I-c)

wherein $R''_2$ represents the same groups as done by $R_2$ except a methyl group, and $R_3$, $R_4$, $R_5$, $R_6$ and $Y$ are as defined above, with a carboxylic anhydride of the formula

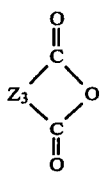 (III-3)

wherein $Z_3$ represents a group $Y_1$, a group of the formula

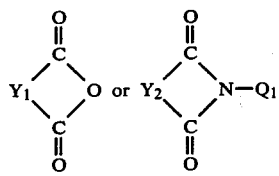

in which $Y_1$, $Y_2$ and $Q_1$ are as defined hereinabove, or its reactive derivative; or (e) reacting a compound of the general formula

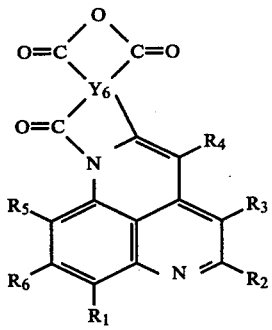 (V)

wherein $R_1$, $R_2$, $R_3$, $R_4$, $R_5$, $R_6$ and $Y_6$ are as defined hereinabove,
with the compound of general formula (II) above; or (f) reacting a compound of the general formula

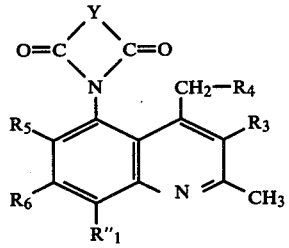 (IV-2)

wherein $R''_1$, $R_3$, $R_4$, $R_5$, $R_6$ and Y are as defined hereinabove,
with a carboxylic anhydride of the formula

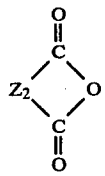 (III-2)

wherein $Z_2$ is as defined above, or its reactive derivative at an elevated temperature.

These alternative methods are described in more detail below.

Method (a)

According to method (a), the amino compound of formula (II) is reacted with the carboxylic anhydride of formula (III-1) or its reactive derivative.

The reaction can be performed in the presence or absence of an inert solvent. Generally, the presence of solvent is advantageous. Such a solvent may be any solvent which will not be involved directly in the reaction. Usually, solvents having a boiling point of at least 100° C. are preferred. Examples of the solvents are hydrocarbons such as decalin, tetraline or trimethylbenzene; halogenated hydrocarbons such as dichlorobenzene, trichlorobenzene or chloronaphthalene; nitrated hydrocarbons such as nitrobenzene; ethers such as diphenyl ether; and N-methylpyrrolidone.

The reaction is carried out generally under heat. The heating temperature can be varied over a wide range according, for example, to the types and proportions of the starting materials, or the type of the solvent. Usually, it is at least 50° C., preferably 100° to 350° C., more preferably 150° to 300° C. The reaction pressure is usually normal atmospheric pressure, but if desired, the reaction may be performed at a reduced or elevated pressure. Within the above temperature range, the reaction ends generally in 1 to 10 hours.

The ratios between the amino compound of formula (II) and the carboxylic anhydride of formula (III-1) or its reactive derivative are not critical, and can be varied over a wide range according, for example, to the types of the starting materials or the reaction conditions. It is generally advantageous that the carboxylic anhydride of formula (III-1) or its reactive derivative is used in an amount at least 0.5 mole, preferably in a somewhat excessive amount (1.2 to 3 moles), especially about 1.5 moles, per mole of the amino compound of formula (II). When a compound of formula (III-1) in which $Z_1$ is

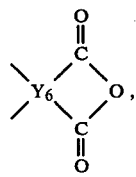

it is advantageous to use the carboxylic anhydride of formula (III-1) or its reactive derivative in an amount of at least 0.2 mole, preferably 0.5 to 4.0 moles, more preferably 1.0 to 3.0 moles, per mole of the amino compound of formula (II). Thus, a compound of formula (I) in which Y is $>Y_6=Q_3$ is obtained in a good yield.

The reaction sufficiently proceeds by heating the two starting materials under the above-described reaction conditions, but as needed, the reaction can be carried out in the presence of an effective amount [usually about 0.001 to 1.0 equivalents per mole of the amino compound of formula (II)] of a Friedel-Crafts catalyst such as zinc chloride, aluminum chloride, antimony pentoxide, iron trichloride, tin tetrachloride, or titanium tetrachloride, boron trifluoride boron trifluoride-dietherate or other dehydrating catalysts such as phosphorus pentoxide, or concentrated sulfric acid. This is especially desirable when the reaction temperature is relatively low, for example not more than about 250° C.

because at such temperatures, the rate of the reaction decreases.

Some of the compounds of formula (II) used as a starting material are known [for example, 5-amino-8-chloro-2,4-dimethyl-quinoline, Yakugaku Zusshi, 70, 389 (1950)]. The novel compounds of formula (II) can be prepared similarly to the production of the known compounds. For example, amino compounds of formula (II) can be produced through a synthetic route shown in the following reaction scheme A utilizing the Doebner-Miller Synthesis.

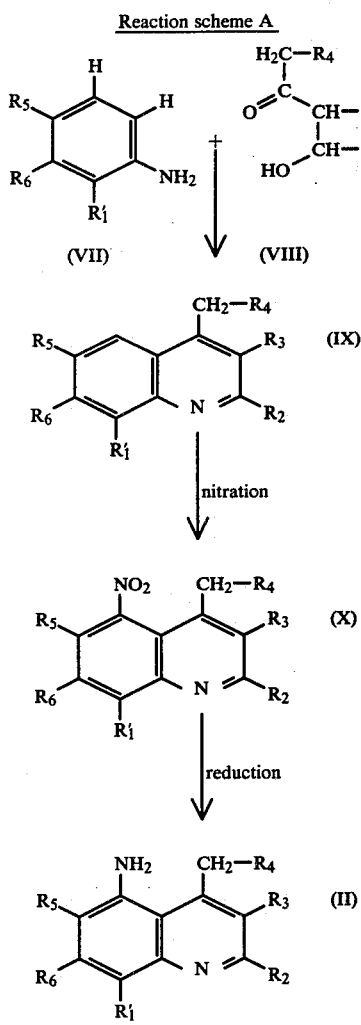

The reaction between the compound of formula (VII) and the compound of formula (VIII) can be carried out under the reaction conditions of the Doebner-Miller synthesis described, for example, in Robert C. Elderfield, "Heterocyclic Compounds," Vol. IV, Chap. I., pages 1 to 344 (1952), published by John Wiley & Sons, Inc. Nitration of the resulting compound of formula (IX) can be performed in a customary manner using mixed acid ($H_2SO_4 + HNO_3$), for example. The nitration product of formula (X) is then reduced by a conventional method, for example by the Bechamp process using Fe/HCl, to afford the amino compound of formula (II) in a good yield.

The amino compound of formula (II) can be produced also by the Riehm's synthesis described in the above cited reference "Heterocyclic Compounds" instead of using the Doebner-Miller synthesis.

Typical examples of the compound of formula (II) used as a starting material in method (a) in accordance with this invention are as follows:

8 (or 6)-Chloro(bromo or fluoro)-5-amino-4-methyl (or ethyl)-quinoline, 8 (or 6)-methyl (or ethyl)-5-amino-4-methyl (or ethyl)-quinaldine, 8 (or 6)-methoxy (or ethoxy)-5-amino-4-methyl (or ethyl)-quinaldine, 8 (or 6)-chloro(bromo or fluoro)-5-amino-3,4-dimethyl-quinaldine, 5-amino-3,8-dimethyl-4-ethyl-quinaldine, 5,8-diamino-4-methyl (ethyl or benzyl)-quinaldine, 5-amino-8-acetylamino(benzylamino, benzoylamino or 4,6-anilino-1,3,5-triazinyl)-4-methyl(ethyl or phenyl)-quinaldine, 5-amino-3,4,6,8-tetramethyl-quinaldine, 8-methoxycarbonyl-4-cyanoethyl-5-amino-quinaldine, 8-chloro(bromo or fluoro)-5-amino-4-(p-aminobenzyl)-quinaldine, 8-hydroxy-5-amino-4-methyl (or ethyl)-quinaldine, 8-hydroxy-5,7-diamino-4-methyl (or ethyl)-quinaldine, 8-trifluoromethyl-5-amino-4-methyl (or ethyl)-quinaldine.

Typical examples of the carboxylic anhydride of formula (III-1) to be reacted with the amino compound of formula (II) are listed below.

Phthalic anhydride,
monochloro(monobromo or fluoro)phthalic anhydride,
dichloro(dibromo or fluoro)phthalic anhydride,
tetrachloro(tetrabromo)phthalic anhydride,
naphthalic anhydride,
3(or 4)-chloronaphthalic anhydride,
3(or 4)-bromonaphthalic anhydride,
naphthalene-2,3-dicarboxylic anhydride,
5,8-dibromo-naphthalene-2,3-dicarboxylic anhydride,
5,6,7,8-tetrabromo-naphthalene-2,3-dicarboxylic anhydride,
naphthalene-1,2-dicarboxylic anhydride,
benzenesulfonyl-naphthalene-2,3-dicarboxylic anhydride,
pyromellitic dianhydride, and
3-chloro-5,7-dimethyl-indeno-[2,1a]-4,12α-diazaphenalen- 12-one-9,10-dicarboxylic anhydride.

Preferred species of the reactive derivative of the carboxylic anhydride are those of the following formula

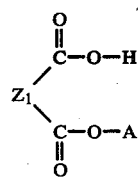

wherein A represents a hydrogen atom or a lower alkyl group,
which are obtained by ring-opening the carboxylic anhydrides of formula (III-1) by hydrolysis or alcoholysis.

Thus, the diazaphenalene derivative of formula (I) can be obtained in a good yield. The compound is separated from the reaction mixture and as needed, purified.

When a methyl group is present at the 2-position of the amino compound of formula (II) or a primary amino group is present at the 8-position of this compound in its reaction with the carboxylic anhydride of formula (III-1) or its reactive derivative, the carboxylic anhydride of formula (III-1) or its reactive derivative reacts not only with the amino group at the 5-position, but also, depending upon the reaction conditions employed, with the methyl group at the 2-position or the primary amino group at the 8-position to afford a compound of formula (I) having a group of the formula

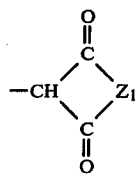

at the 2-potition (when methyl is at the 2-position), or a compound of formula (I) having a group of the formula

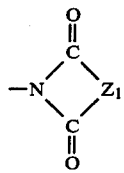

at the 8-position (when primary amino is present at the 8-position).

When the production of such a compound of formula (I) is intended, it is desirable, contrary to the foregoing description, to use the amino compound of formula (II) in an amount of at least 1.5 moles, preferably 2.0 to 4.0 moles, per mole of the carboxylic anhydride of formula (III-1) or its reactive derivative.

When it is desired to obtain a compound of formula (I) in which $R_1$ is a primary amino group ($-NH_2$), it is desirable, prior to the reaction between a compound of formula (II) in which $R'_1$ is a primary amino group and the carboxylic anhydride of formula (III-1) or its reactive derivative, to protect the amino group temporarily by a conventional amino-protecting group capable of being easily split off.

Method (b)

When the reaction between the amino compound of formula (II) and the carboxylic anhydride of formula (III-1) or its reactive derivative is carried out under mild conditions, for example at a relatively low heating temperature in the absence of a catalyst, the compound of formula (IV-1) that can be used as a starting material in method (b) can be advantageously formed.

The heating temperature used to form the compound of formula (IV-1) advantageously differs widely according, for example, to the type of the amino compound of formula (II) and/or the carboxylic anhydride of formula (III-1) or its reactive derivative, and the type of the solvent used, and cannot be determined definitely. Generally, the temperature is not more than 250° C., preferably 100° to 250° C., more preferably 150° to 200° C.

Some of the compounds of formula (II) react to the extent of forming compounds of formula (I) at a relatively high temperature within the above-specified temperature range. In such a case, the compound of formula (IV-1) can be advantageously formed by using lower heating temperatures near the lower limit of the above-specified temperature range. Any person skilled in the art would be able to easily determine the heating temperature for a given compound of formula (II) by a small-scale laboratory experiment.

The reaction time in this reaction also varies according to the type of the amino compound of formula (II) and/or the carboxylic anhydride of formula (III-1) or its reactive derivative, and cannot be determined definitely. However, since too long a reaction time is likely to cause the formation of the compound of formula (I), it is usually preferred to restrict it within the range of 1 to 5 hours.

The resulting compound of formula (IV-1) may be subjected to a cyclization reaction directly or after having been separated from the reaction mixture.

According to method (b), the resulting compound of formula (IV-1) can be cyclized to the final product of formula (I) by dehydration.

The cyclization reaction may be carried out in the presence or absence of a solvent. Usually, it is advantageous to perform the cyclization in an inert organic solvent of the type described hereinabove with regard to method (a).

The heating temperature for the heat cyclization reaction of the compound of formula (IV-1) differs widely according to the type of the compound of formula (IV-1) used as a starting material or the type of the solvent used, and cannot be set definitely. Generally, the advantageous temperature is at least 150° C., preferably 170° to 300° C., and more preferably 200° to 270° C. In any case, it is very desirable to use temperatures higher than those used to form the compound of formula (IV-1) by the reaction of the amino compound of formula (II) with the carboxylic acid anhydride of formula (III-1) or its reactive derivative.

The cyclization reaction sufficiently proceeds usually under atmospheric pressure, but as needed, reduced or elevated pressures may be employed.

The cyclization reaction proceeds sufficiently satisfactorily in the absence of catalyst. As needed, the reaction may be carried out in the presence of an effective amount [usually, about 0.001 to 1.0 equivalent per mole of the compound of formula (IV-1)] of a Friedel-Crafts catalyst of the type described hereinabove. The use of such a catalyst is frequently effective when the rate of the cyclization reaction is slow.

Under the reaction conditions described, the cyclization reaction can be terminated usually within 1 to 10 hours, to afford the compound of formula (I) in good yields.

Method (c)

When a compound of formula (I) in which $R_2$ is a methyl group [i.e., a compound of formula (I-b) in which an active methyl group is bonded to the α-position of the quinoline ring] which can be obtained by method (a) or (b) is reacted with a carboxylic anhydride of the formula

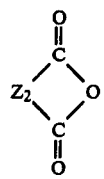 (III-2)

wherein $Z_2$ is as defined hereinabove,
or its reactive derivative, the methyl group reacts with the carboxylic anhydride of formula (III-2) or its reactive derivative to form a compound of formula (I) in which $R_2$ corresponds to

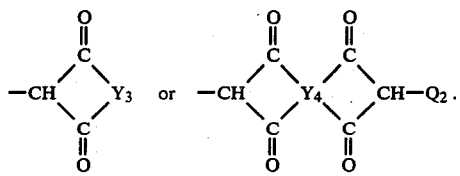

The reaction in accordance with method (c) between the compound of formula (I-b) and the carboxylic anhydride of formula (III-2) or its reactive derivative can be carried out under substantially the same reaction conditions as described hereinabove with regard to method (a).

The compound of formula (I-b) can be prepared, for example, by reacting an amino compound of formula (II) in which $R_2$ is a methyl group with the carboxylic anhydride of formula (III-1) or its reactive derivative under relatively mild conditions by method (a); or by synthesizing a compound of formula (IV-1) in which $R_2$ is a methyl group by method (b), and then treating it in accordance with method (b).

The reaction between the compound of formula (I-b) and the carboxylic anhydride of formula (III-2) or its reactive derivative is carried out at a relatively high temperature. The heating temperature widely differs according, for example, to the type of the compound of formula (I-b) and/or the carboxylic anhydride of formula (III-2) or its reactive derivative, and cannot be set definitely. Generally, the temperature is advantageously 150° to 300° C., preferably 200° to 270° C.

The carboxylic anhydride of formula (III-2) or its reactive derivative to be reacted with the compound of formula (I-b) is selected from those carboxylic anhydrides of formula (III-1) or their reactive derivatives which are exemplified hereinabove. There can also be used dichloro-naphthalene-1,2-dicarboxylic anhydride,
p-chloro-benzenesulfonyl-2,3-naphthalene-dicarboxylic anhydride,
diphenic anhydride, and
diphenylsulfone-3,4,3',4'-tetracarboxylic dianhydride.

When in the reaction of the compound of formula (I-b) with the carboxylic anhydride of formula (III-2) or its reactive derivative, $R''_1$ in formula (I-b) is a primary amino group, the carboxylic anhydride of formula (III-2) or its reactive derivative attacks this amino group to form compounds of formula (I) in which $R_2$ represents

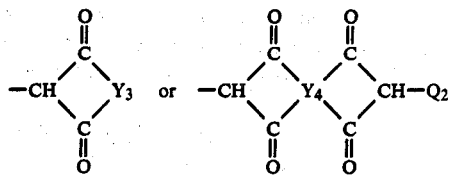

and at the same time, $R_1$ represents

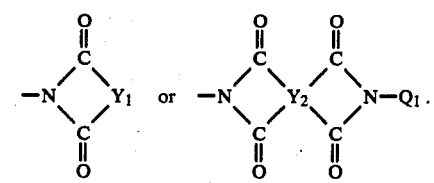

Method (d)

Reaction of a compound of formula (I) in which $R_1$ is a primary amino group and $R_2$ is any of the groups defined hereinabove except methyl [i.e., a compound of formula I-c)] with a carboxylic anhydride of the formula

 (III-3)

wherein $Z_3$ is as defined hereinabove, or its reactive derivative can afford a compound of formula (I) wherein $R_1$ represents

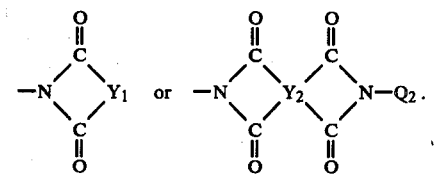

The reaction of the compound of formula (I-c) with the carboxylic anhydride of formula (III-3) or its reactive derivative can be performed either in the presence or absence of a solvent. When a solvent is used, inert organic solvents exemplified hereinabove with regard to method (a) can be used.

The reaction between the compound of formula (I-c) and the carboxylic anhydride of formula (III-3) or its reactive derivative can be performed easily by heating both of them. The heating temperature is not critical, and can be varied widely according, for example, to the type of the compound of formula (I-c) and/or the compound of formula (III-3) or its reactive derivative. Generally, the heating temperature is at least 120° C., preferably 150° to 300° C., more preferably 170° to 270° C.

The reaction can be performed under atmospheric pressure, but as needed, under elevated or reduced pressures.

The ratios between the compound of formula (I-c) and the carboxylic anhydride of formula (III-3) or its reactive derivative are not critical, and can be varied widely. Usually, the amount of the carboxylic anhydride of formula (III-3) or its reactive derivative is at least 0.2 mole, preferably 0.5 to 4.0 moles, more preferably 1.0 to 3.0 moles, per mole of the compound of formula (I-c).

Usually, a catalyst is not required, but if desired, the reaction can be carried out in the presence of a Friedel-Crafts catalyst of the type described hereinabove.

The carboxylic anhydride of formula (III-3) or its derivative used as a starting material in the above reaction can be selected from those carboxylic anhydrides of formula (III-1) or their reactive derivatives which are exemplified hereinabove. There can also be used trimellitic anhydride, and 1,4,5,8-naphthalenetetracarboxylic dianhydride.

Method (e)

By reacting a compound of the following formula

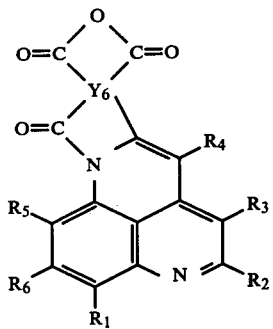

(V)

wherein $R_1$, $R_2$, $R_3$, $R_4$, $R_5$, $R_6$ and $Y_6$ are as defined hereinabove,
which can be prepared by method (a) or (b) under properly controlled reaction conditions, with the amino compound of formula (II), a compound of formula (I) in which Y represents $>Y_6=Q_3$ can be prepared.

The reaction of the compound of formula (V) with the compound (II) can also be carried out either in the presence or absence of a solvent. The inert organic solvents exemplified above with regard to method (a) can be used as the solvent.

The reaction can be performed by heating the two starting materials. The heating temperature is advantageously at least 150° C., preferably 170° to 300° C., more preferably 200° to 270° C. It is sufficient that the reaction pressure is normal atmospheric pressure.

The ratio of the compound of formula (II) to the compound of formula (V) is not critical, and can be varied widely as needed. Generally, the suitable amount of the compound of formula (II) is at least 0.5 mole, preferably 0.8 to 2.0 moles, more preferably 1.0 to 1.5 moles, per mole of the compound of formula (V).

The above reaction can be terminated under these conditions in 1 to 10 hours. Thus, compounds of formula (I) in which Y represents a group of the formula $>Y_6=Q_3$ in good yields.

Method (f)

By reacting a compound of formula (IV-1) used as a starting material in method (b) in which $R_2$ is a methyl group, that is, a compound of the formula

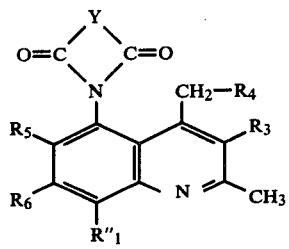

(IV-2)

wherein $R''_1$, $R_2$, $R_3$, $R_4$, $R_5$, $R_6$ and Y are as defined hereinabove, with a carboxylic anhydride of the formula

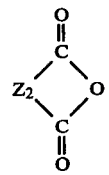

(III-2)

wherein $Z_2$ is as defined hereinabove, or its reactive derivative, a compound of formula (I) in which $R_2$ represents

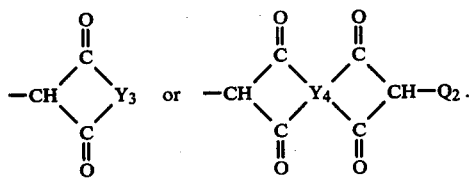

The reaction of the compound of formula (IV-2) with the carboxylic anhydride of formula (III-2) or its reactive derivative can be performed under quite the same conditions as employed in method (c).

The compound of formula (I) obtained by any of the methods (a), (b), (c), (d), (e) and (f) described above can be separated from the reaction mixture by any known method, and as needed, further purified. For example, the reaction mixture after the reaction is cooled, and the resulting precipitate is separated and recovered by, for example, filtration or centrifugal separation. The compound of formula (I) so recovered has a sufficiently high purity, and can be used in applications to be described below. It may, if desired, be further purified by washing with an organic solvent, for example, alcohols such as methanol or ethanol, isopropanol; ketones such as acetone or methylethyl ketone; amides such as dimethyl formamide, N-methylpyrrolidone or dimethylacetamide; halogenated aromatic hydrocarbons such as dichlorobenzene, trichlorobenzene or α-chloronaphthalene.

The compound of formula (I) can be subjected to a pigment-forming treatment by a method known in the art of pigment chemistry. For example, the compound is dissolved in conc. sulfuric acid, and the solution is poured into water to re-precipitate the compound in the form of a fine powder. Or the compound is finely pulverized by a pulverizer such as a ball mill.

The compound can be used as surface-coated with a resin such as polyesters, polycarbonates, polystyrene, polyacrylonitrile, polyvinyl chloride, polyethylene, polypropylene, poly(methyl methacrylate), an ethylene/vinyl acetate copolymer or polyamide, and an inorganic material such as sodium silicate. It may also be used as treated with a silane coupling agent such as γ-methacryloxypropyl trimethoxysilane or γ-aminopropyltriethoxysilane.

The compounds of formula (I), especially (I-a), provided by the present invention have orange to reddish violet colors according to the types of the substituents, and have superior advantages such as superior thermal stability and weatherability, and superior dispersibility especially in polymeric materials. Furthermore, when dispersed in polymeric materials, they do not adversely affect the dimensional stability of the resulting composition, and also have high resistance to migration. These properties enable the compounds to be advantageously used as a coloring component of orange to reddish violet organic pigments.

The compounds of formula (I) of this invention are useful as orange to reddish violet organic pigments, and just the same as ordinary organic pigments, can be used in a wide range of applications, for example, for coloring polymeric shaped articles, or as coloring components of paints, printing inks, crayon, painting pastes or textile printing pastes.

In particular, the compounds of formula (I) of this invention can be advantageously used for coloring polymeric materials. Examples of such polymeric materials include polyolefins such as polyethylene, polypropylene, an ethylene-propylene, copolymer, polystyrene, polybutadiene, an acrylonitrile-butadiene-styrene copolymer (ABS resin) poly(methyl methacrylate), polyvinyl chloride, polyvinyl acetate, or an ethylene-vinyl acetate copolymer, polyamides such as Nylon-6, Nylon-66 or Nylon-12, polyesters such as polyethylene terephthalate or polybutylene terephthalate, polyacetal resins such as polyoxymethylene, polycarbonate resins such as polymers derived from 4,4'-dihydroxydiphenyl-2,2-propane and diphenyl carbonate, amino resins such as melamine, regenerated celluloses such as cellulose triacetate, epoxy resins such as polymers derived from 4,4'-dihydroxydiphenyl-2,2-propane and epichlorohydrin, phenolic resins such as polymers derived from phenol and formaldehyde, urea resins such as polymers derived from urea and formaldehyde, and polyamide resins such as polymers derived from pyromellitic dianhydride and m-phenylenediamine.

In the present specification and the appended claims, the term "polymeric material" is meant to include not only spaced articles prepared from the above resins, but also compositions containing these resins as a binder, carrier, vehicle or the like, for example paints, printing inks and textile printing pastes.

One procedure available for coloring a shaped article of a resin using the compound of formula (I) comprises incorporating the compound of formula (I) in a desired amount (for example, 0.05 to 1 part by weight, preferably 0.1 to 0.5 part by weight, per 100 parts by weight of the resin) in the resin, melting or melt-kneading the blend, and fabricating it into a desired shape such as a film, sheet, plate, pipe, tube, filament, or pellet by a conventional resin fabricating method such as compression molding, injection molding, calendering, or extrusion. According to another method, the compound of formula (I) is incorporated in advance in monomers or prepolymers for forming the resin, and the mixture is polymerized and fabricated to form a colored shaped article of the resin in the above-mentioned form (the cast shaping method).

The compound of formula (I) can also be used to color fibers, woven or knitted fabrics, or nonwoven fabrics. It can be applied by a dip dyeing method same as in the case of disperse dyes, or by a textile printing technique.

The following Examples illustrate the present invention in more detail. All "parts" in these examples are "parts by weight".

EXAMPLE A-1

Thirty parts of 5-amino-8-ethyl-2,4-dimethylquinoline, 42.9 parts of tetrachlorophthalic anhydride and 200 parts of o-dichlorobenzene were reacted under reflux for 3.5 hours at the boiling point. After cooling, the reaction mixture was filtered, washed with alcohol, and dried to afford 43.4 parts of a red reaction product having the following structural formula:

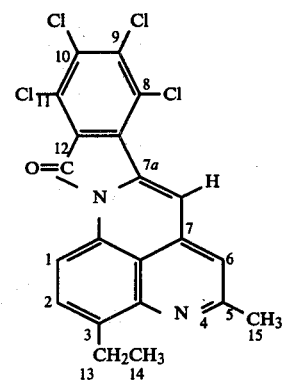

This product had a melting point of 322° to 324° C., and its visible absorption spectrum in an α-chloronaphthalene solution showed maximum values of 512 and 485 mμ.

In its infrared absorption spectrum, a characteristic absorption due to the carbonyl group at the 12-position was observed at 1705 cm$^{-1}$.

In its mass spectrum, M+ m/e 450, a parent peak corresponding to $C_{21}H_{12}N_2OCl_4$, was observed.

The elemental analysis values as found were C:55.87%, H:2.67%, and N:6.31%, which well corresponded with the calculated values C:56,00%, H:2.67%, N:6,22%.

The main peaks of $13_c$ NMR in $H_2SO_4$ were as follows:

| | | |
|---|---|---|
| —CH$_2$CH$_3$ | (C-14) | 13.167 ppm |
| —CH$_3$ | (C-15) | 21.897 ppm |
| —CH$_2$CH$_3$ | (C-13) | 23.360 ppm |
| \C/ \H | (C-7) | 112.658 ppm |
| =C\ / | (C-7a) | 101.394 ppm |
| \C=O / | (C-12) | 164.552 ppm |

EXAMPLES A-2 to A-5

In these examples, Example A-1 was repeated except that 5-amino-8-ethyl-2,4-dimethylquinoline and tetrachlorophthalic anhydride were changed to the compounds described below.

Diazaphenalene derivatives of the formula

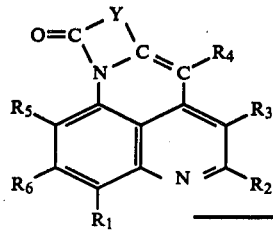

were prepared by reacting 5-aminoquinolines of the formula

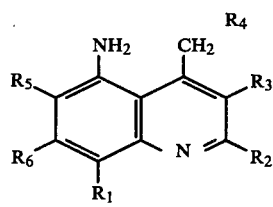

wherein $R_1$, $R_2$, $R_3$, $R_4$, $R_5$ and $R_6$ are shown in Table A below,
with dicarboxylic anhydrides of the formula

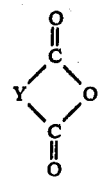

wherein Y is shown in Table A below, in the same way as in Example A-1.

The infrared absorption spectra and the visible absorption spectra of the products are shown in Table A.

In the following tables, α-chloronaphthalene is abbreviated as α-CN, and dimethyl formamide, as DMF.

Table A

| Example | $R_1$ | $R_2$ | $R_3$ | $R_4$ | $R_5$ | $R_6$ | Y | IR characteristic absorption $(cm^{-1})$ | Absorption maximum in the visible region $[\lambda max \cdot (m\mu)]$ |
|---|---|---|---|---|---|---|---|---|---|
| A-2 | Br | $CH_3$ | H | $CH_3$ | H | H | phenyl | 1695 | 473 (α-CN) |
| A-3 | Cl | $CH_3$ | H | $CH_3$ | H | H | phenyl | 1700 | 475 (shoulder) 459 (α-CN) |
| A-4 | Cl | H | H | H | H | H | tetrachlorophenyl | 1710 | 444 (DMF) |
| A-5 | $CH_3$ | $CH_3$ | H | H | H | H | tetrachlorophenyl | 1712 | 483 (DMF) |

EXAMPLE B-1

115.7 Parts of 5-amino-8-chloro-4-ethyl-2-methylquinoline, 74 parts of phthalic anhydride and 250 parts of α-chloronaphthalene were reacted at 250° C. for 2 hours. After cooling, the reaction mixture was filtered, and washed with acetone to afford 158.1 parts of an orange solid having the following structural formula:

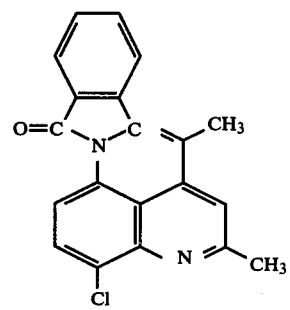

The product had a melting point of 323° C. In its infrared absorption spectrum, the absorption of carbonyl was seen at 1700 cm$^{-1}$. Its mass spectrum showed m/e 322.0682 and 334.0665 corresponding to $C_{20}H_{13}N_2OCl$. The maximum wavelengths of its visible absorption spectrum in an α-chloronaphthalene solution were 475 mμ (shoulder), and 459 mμ.

EXAMPLE B-2

A compound of the following structural formula was synthesized in the same way as in Example B-1 except that 99 parts of naphthalene-1,8-dicarboxylic anhydride was used instead of 74 parts of phthalic anhydride.

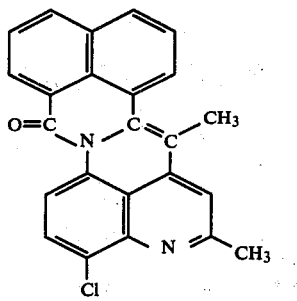

This compound showed the following characteristics.

In its infrared absorption spectrum, the absorption of carbonyl was seen at 1710 and 1720 cm$^{-1}$. Its mass spectrum showed a parent peak corresponding to $C_{24}H_{15}N_2OCl$ at m/e 382. The maximum wavelengths of its visible absorption spectrum in an α-chloronaphthalene solution were 475 mμ (shoulder) and 435 mμ.

EXAMPLE C-1

120.9 Parts of 5-amino-2,4,8-trimethylquinoline, 96.2 parts of phthalic anhydride and 975 parts of o-dichlorobenzene were reacted under reflux for 2.5 hours. The reaction mixture was cooled, filtered, and washed with diethyl ether to afford 108.2 parts of a white solid.

The product had a melting point of 228° to 230° C. In its infrared absorption spectrum, the absorption of carbonyl was seen at 1790, 1775 and 1720 cm$^{-1}$. Its mass spectrum showed m/e 316.1207 corresponding to $C_{20}H_{16}N_2O_2$. No absorption was seen in the visible region in its visible absorption spectrum in an α-chloronaphthalene solution. The peaks of its NMR spectrum in $CDCl_3$ were δ(ppm) 2.40 (3H, s), 2.62 (3H, s), 2.82 (3H, s), and 7-8 (7H, m).

From the above results of analyses, the product was determined to be a compound of the following formula:

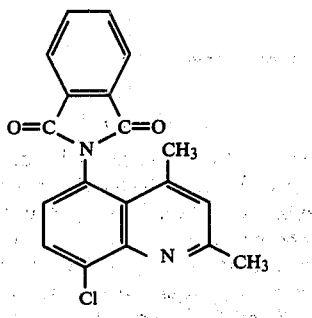

EXAMPLE C-2

Twenty parts of the 5-phthalimide-2,4,8-trimethylquinoline obtained by the reaction in Example C-1 was heated in 50 parts of α-chloronaphthalene to 240°-250° C. for 2 hours. The reaction mixture was cooled, filtered, and washed with acetone to afford 16.5 parts of an orange solid.

The product had a melting point of 315°to 316° C. In its infrared absorption spectrum, the absorption of carbonyl was seen at 1710 cm$^{-1}$. Its mass spectrum showed m/e 298.1081 corresponding to $C_{20}H_{14}N_2O$. The maximum wavelength of its visible absorption spectrum in an α-chloronaphthalene solution was 470 mμ.

From the above results of analyses, the product was determined to be a compound of the following structural formula:

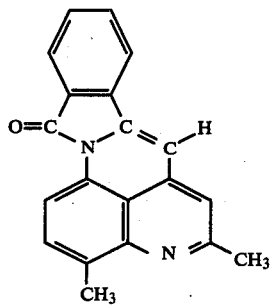

EXAMPLE C-3

16.4 Parts of the 5-phthalimide-2,4,8-trimethylquinoline obtained in Example C-1, 23.6 parts of tetrachlorophthalic anhydride and 22 parts of α-chloronaphthalene were reacted at 240° C. for 2.5 hours. Then, the reaction mixture was filtered at 120° C., and washed twice with 200 parts of α-chloronaphthalene at an elevated temperature, twice with 150 parts of dimethylformamide, and then twice with 200 parts of acetone to afford 18.1 parts of a red compound having the following structural formula:

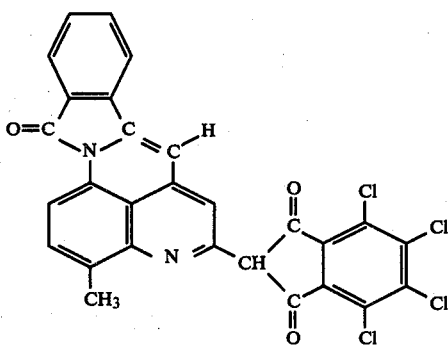

In its infrared absorption spectrum, an absorption was seen at 1730 cm$^{-1}$, and the maximum wavelengths of its visible absorption spectrum in an α-chloronaphthalene solution were 528 mμ and 497 mμ.

EXAMPLES C-4 TO C-6

In these Examples, the procedure of Example C-3 was repeated using the following compounds instead of the 2-methylquinoline derivative and tetrachlorophthalic anhydride used in Example C-3.

Specifically, a 2-methylquinoline derivative of the formula:

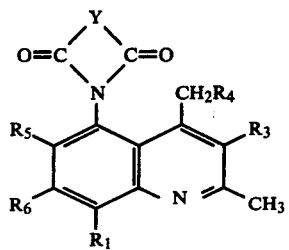

wherein $R_1$, $R_3$, $R_4$, $R_5$, $R_6$ and Y are as shown in Table B below,
was reacted in the same way as in Example C-3 with a dicarboxylic anhydride of the formula

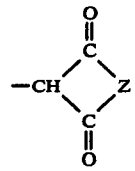

wherein Z is as shown in the column of $R_2$ in Table B as to afford a compound of the following formula

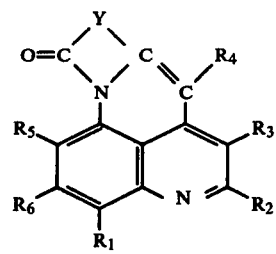

wherein $R_2$ is as shown in Table B.

The infrared absorption spectra and the visible absorption spectra of the products are shown in Table B.

Table B

| Ex. | $R_1$ | $R_2$ | $R_3$ | $R_4$ | $R_5$ | $R_6$ | Y | IR characteristic absorption (cm$^{-1}$) | Absorption maximum in the visible region [$\lambda$max. (m$\mu$)] |
|---|---|---|---|---|---|---|---|---|---|
| C-4 | F | (tetrachlorophthalimide-CH group) | H | CH$_3$ | H | H | (benzene ring) | 1760 1730 | 535 ($\alpha$-CN) |
| C-5 | —NHCOCH$_3$ | (tetrachlorophthalimide-CH group) | H | H | H | H | (benzene ring) | 1735 1710 | 532 ($\alpha$-CN) |
| C-6 | (N,N'-diphenyl melamine-NH group) | (tetrachlorophthalimide-CH group) | H | H | H | H | (benzene ring) | 1730 | 566 (shoulder) 520 ($\alpha$-CN) |

EXAMPLE C-7

14.9 Parts of the 3,5-dimethyl-indeno-[2,1a]-4,12a-diazaphenalen-12-one obtained in Example C-2, 21.5 parts of tetrachlorophthalic anhydride and 75 parts of α-chloronaphthalene were reacted at 240° to 250° C. for 3 hours, filtered at 120° C., and washed first with 200 parts of α-chloronaphthalene and then with 200 parts of acetone to afford 25.9 parts of a red compound. This compound corresponded with the compound obtained in Example C-3.

EXAMPLES C-8 TO C-14

In these Examples, the procedure of Example C-7 was repeated except that the following compounds were used instead of the diazaphenalene derivative and tetrachlorophthalic anhydride used in Example C-7.

Specifically, a 5-methyldiazaphenalene derivative of the formula

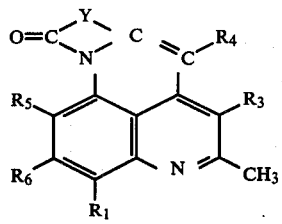

wherein $R_1$, $R_3$, $R_4$, $R_5$, $R_6$ and Y are as shown in Table C below,
was reacted in the same way as in Example C-7 with a dicarboxylic anhydride of the formula

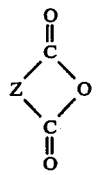

wherein Z is as shown in the column of $R_2$ in Table C as

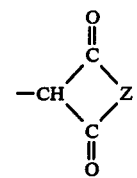

to afford a compound of the formula

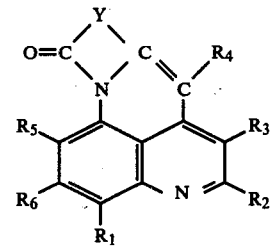

wherein $R_2$ is as shown in Table C.

The infrared absorption spectra and visible absorption spectra are shown in Table C.

Table C

| Example | $R_1$ | $R_2$ | $R_3$ | $R_4$ | $R_5$ | $R_6$ | Y | IR characteristic absorption (cm$^{-1}$) | Absorption maximum in the visible region [$\lambda$max . (m$\mu$)] |
|---|---|---|---|---|---|---|---|---|---|
| C-8 | Cl | ![tetrachlorophthalic CH group] | H | CH$_3$ | H | H | benzene | 1720 | 534 502 ($\alpha$-CN) |
| C-9 | Cl | ![tetrachlorophthalic CH group] | H | CH$_3$ | H | H | naphthalene (1,8) | 1740 | 540 (shoulder) 500 ($\alpha$-CN) |
| C-10 | CH$_3$ | ![tetrachlorophthalic CH group] | CH$_3$ | H | H | H | benzene | 1732 | 552 514 ($\alpha$-CN) |
| C-11 | CH$_3$ | ![tetrachlorophthalic CH group] | CH$_3$ | H | H | H | naphthalene (2,3) | 1725 | 551 513 ($\alpha$-CN) |

Table C-continued

| Example | R$_1$ | R$_2$ | R$_3$ | R$_4$ | R$_5$ | R$_6$ | Y | IR characteristic absorption (cm$^{-1}$) | Absorption maximum in the visible region [λmax . (mμ)] |
|---|---|---|---|---|---|---|---|---|---|
| C-12 | CH$_3$ | 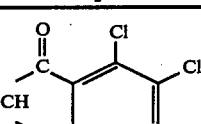 | CH$_3$ | H | H | H | 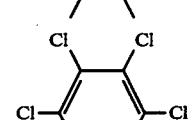 | 1742 | 553 517 (α-CN) |
| C-13 | CH$_3$ | 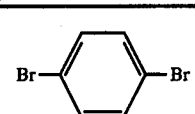 | H | H | H | H | 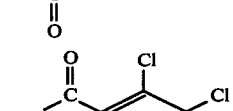 | 1722 | 515 (DMF) |
| C-14 | Br | 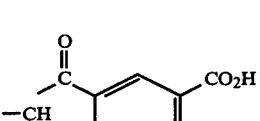 | H | CH$_3$ | H | H | 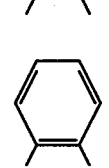 | 1730 | 534 (α-CN) |

EXAMPLE C-15

93 Parts of 5-amino-2,4,8-trimethylquinoline, 81.5 parts of phthalic anhydride and 750 parts of α-chloronaphthalene were reacted at 180° C. for 2 hours and then at 240° to 250° C. for 3 hours. Then, 214.5 parts of tetrachlorophthalic anhydride was added, and the reaction was performed at 240° to 250° C. for an additional 3 hours. The reaction mixture obtained was filtered at 120° C., and washed twice with 200 parts of α-chloronaphthalene at an elevated temperature and then twice with 200 parts of acetone to afford 222 parts of a red compound. This compound corresponded with the compounds obtained in Examples C-3 and C-7.

EXAMPLES C-16 TO C-22

In these Examples, the procedure of Example C-15 was repeated except that the following compounds were used instead of the 5-amino-2,4,8-trimethylquinoline, phthalic anhydride and tetrachlorophthalic anhydride.

Specifically, a 5-amino-2-methylquinoline of the formula

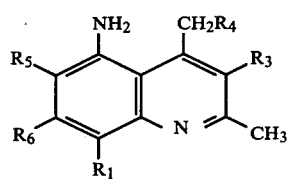

wherein R$_1$, R$_3$, R$_4$, R$_5$ and R$_6$ are shown in Table D, was reacted in the same way as in Example C-15 with a dicarboxylic anhydride of the following formula

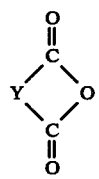

wherein Y is as shown in Table D, and then further reacted with a dicarboxylic anhydride of the following formula

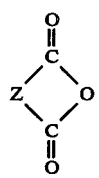

wherein Z is shown in the column of R$_2$ in Table D as

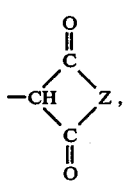

to afford a compound of the following formula

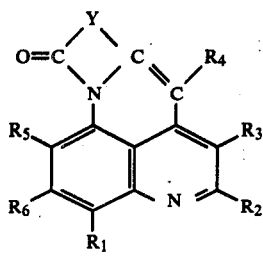

wherein R₂ is as shown in Table D.

The infrared absorption spectra and the visible absorption spectra of the resulting compounds are shown in Table D.

was neutralized with oxalic acid, and the sodium oxalate that precipitated was removed by filtration. The unreacted methyl ethyl ketone was evaporated off by an evaporator to afford 1515 parts of a reaction product containing about 24% of 5-hydroxy-3-hexanone.

(2)—507 Parts of o-toluidine was dissolved in 1382 parts of 35% hydrochloric acid, and at 81° to 83° C., 1505 parts of the reaction product obtained in (1) above was added over the course of 75 minutes. The mixture was stirred for one hour. The reaction mixture obtained was cooled, neutralized with a 40% aqueous solution of sodium hydroxide, extracted with ether, and distilled under reduced pressure. The fractions having a boiling point of 105° to 120° C./0.17 mmHg were collected to afford 397 parts of 2,8-dimethyl-4-ethyl quinoline (purity 82% by weight).

Table D

| Example | R₁ | R₂ | R₃ | R₄ | R₅ | R₆ | Y | IR characteristic absorption (cm⁻¹) | Absorption maximum in the visible region [λmax. (mμ)] |
|---|---|---|---|---|---|---|---|---|---|
| C-16 | CH₃ | -CH(C(=O))₂C₆Cl₄ | H | CH₃ | H | H | o-xylyl | 1729 | 490 (DMF) |
| C-17 | CH₃ | -CH(C(=O))₂C₆Cl₄ | H | CH₃ | H | H | 2,7-dibromonaphthyl | 1740 | 538, 505 (α-CN) |
| C-18 | CH₃ | -CH(C(=O))₂C₆Cl₄ | H | CH₃ | H | H | naphthyl | 1735 | 470 (DMF) |
| C-19 | OCH₃ | -CH(C(=O))₂C₆Cl₄ | H | CH₃ | H | H | o-xylyl | 1725 | 520 (α-CN) |
| C-20 | CH₃ | -CH(C(=O))₂C₆Br₄ | H | H | H | H | tetrachloroxylyl | 1730 | 555, 515 (α-CN) |
| C-21 | CH₃ | -CH(C(=O))₂C₆Cl₄ | H | H | H | H | tetrabromoxylyl | 1730 | 553, 516 (α-CN) |
| C-22 | H | -CH(C(=O))₂C₆Cl₄ | H | H | OH | H | o-xylyl | 1695 | 505 (α-CN) |

EXAMPLE C-23

(1)—Methyl ethyl ketone (5040 parts), 14 parts of sodium hydroxide, 14 parts of water and 56 parts of methanol were stirred, and 616 parts of acetaldehyde (purity 85% by weight) was added at 32° to 33° C. over the course of 35 minutes. At this temperature, the stirring was continued for 10 minutes. The reaction mixture (3)—383 Parts of the 2,8-dimethyl-4-ethylquinoline (purity 82% by weight) obtained in (2) above was dissolved in 999 parts of conc. sulfuric acid. While the solution was maintained at below 20° C., a mixture of 285 parts of fuming nitric acid (d:1.50) and 350 parts of conc. sulfuric acid was added over the course of 2 hours. The stirring was continued for an additional 15 minutes. The reaction mixture was put into 5000 parts of ice water, and filtered. The filtrate was neutralized with a 40% aqueous solution of sodium hydroxide. The precipitated crystals were separated by filtration, and recrystallized from methanol to afford 5-nitro-2,8-dimethyl-4-ethylquinoline as crystals having a purity of 99% by weight and a melting point of 89° to 90° C.

| NMR spectrum (CDCl₃/TMS): δ (ppm) | |
|---|---|
| 1.25 (3H, t) | —CH₂CH₃ |
| 2.68 (3H, s) | —CH₃ |
| 2.76 (3H, s) | —CH₃ |
| 2.80 (2H, q) | —CH₂CH₃ |
| 7.2–7.6 (3H, m) | phenyl proton |

High-resolution mass spectrum: m/e

M+ 230.1041 ($C_{13}H_{14}N_2O_2$)

(4)—With vigorous stirring, 230 parts of the 5-nitro-2,8-dimethyl-4-ethylquinoline (purity 99% by weight) obtained in (3) above was added to a mixture consisting of 168 parts of iron powder, 36 parts of 35% hydrochloric acid, 100 parts of water and 600 parts of methanol at 60° C. over the course of 1 hour. After the addition, the stirring was continued under reflux for 2 hours. The reaction mixture obtained was neutralized with a 30% aqueous solution of sodium hydroxide, and hot filtered. The filtrate was extracted with diethyl ether, dried over sodium sulfate, and distilled under reduced pressure to afford 177.1 parts of 5-amino-2,8-dimethyl-4-ethylquinoline having a purity of 97% by weight.

Melting point: 60° to 62° C.

| NMR spectrum (CDCl₃/TMS): δ(ppm) | |
|---|---|
| 1.28 (3H, t) | —CH₂CH₃ |
| 2.58 (3H, s) | —CH₃ |
| 2.64 (3H, s) | —CH₃ |
| 3.10 (2H, q) | —CH₂CH₃ |
| 3.95 (2H, s) | —NH₂ |
| 6.44 (1H, d) | phenyl proton |
| 6.80 (1H, s) | phenyl proton |
| 7.16 (1H, d) | phenyl proton |

High-resolution mass spectrum: m/e

M+ 200.1264 ($C_{13}H_{16}N_2$)

(5)—19.8 Parts of 2,3-naphthalenedicarboxylic anhydride was dissolved in 163 parts of α-chloronaphthalene, and 20.1 parts of the 5-amino-2,8-dimethyl-4-ethylquinoline obtained in (4) above was added and reacted at 150° C. for 1 hour. Then, 57.2 parts of tetrachlorophthalic anhydride was added, and the reaction was performed at 240° C. for 3 hours. The reaction mixture was filtered at 200° C., and washed twice with dimethyl formamide and then twice with acetone to afford 48.3 parts of a reddish orange solid having the following structural formula:

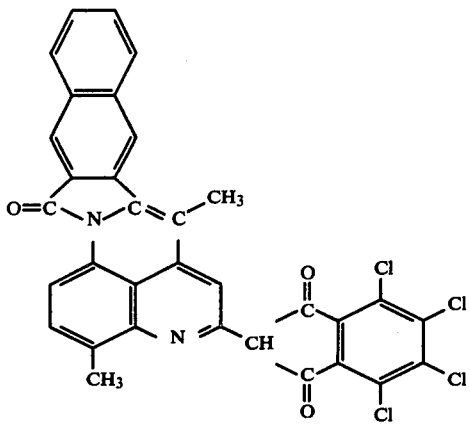

The product had a melting point of more than 360° C. The maximum wavelength of its visible absorption spectrum in a dimethyl formamide solution was 490 mμ. Its infrared absorption spectrum showed the absorption of carbonyl at 1735 $cm^{-1}$ and 1678 $cm^{-1}$.

The elemental analysis values were as follows:

|  | C | H | N |
|---|---|---|---|
| Found (%): | 62.19 | 2.24 | 4.02 |
| Calculated (%): | 62.88 | 2.56 | 4.45 |

EXAMPLE D

196 Parts of 5-amino-8-chloro-2,4-dimethylquinoline and 286 parts of tetrachlorophthalic anhydride were heated for 3 hours in 1000 parts of trichlorobenzene. Then, 198 parts of naphthalic anhydride and 35 parts of zinc chloride were added, and the mixture was heated for 4 hours. The reaction mixture was cooled, and filtered. The crystals separated were washed with 500 parts of hot dimethyl formamide to afford 470 parts of a red solid having the following structural formula:

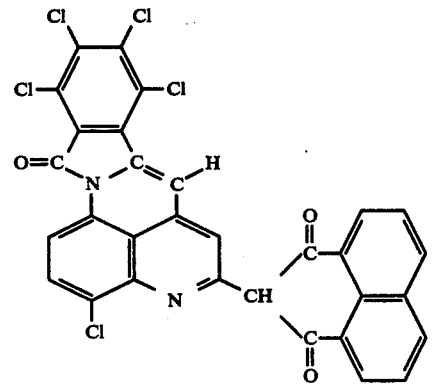

Melting point: above 360° C.

Infrared absorption spectrum: 1712 $cm^{-1}$

Maximum absorption in its visible spectrum in a α-chloronaphthalene solution: 550 mμ

EXAMPLE E-1

70 Parts of 8-chloro-5-amino-2,4-dimethylquinoline, 250 parts of tetrachlorophthalic anhydride and 15 parts of zinc chloride and 1000 parts of trichlorobenzene were reacted under reflux for 4 hours at the boiling point. Then, 250 parts of dimethyl formamide was added, and the mixture was stirred for 1 hour under reflux. After cooling, the reaction mixture was filtered. The red reaction product was washed with 500 parts of dimethyl formamide and then with ethanol, and dried to afford 180 parts of a red solid having the following structural formula:

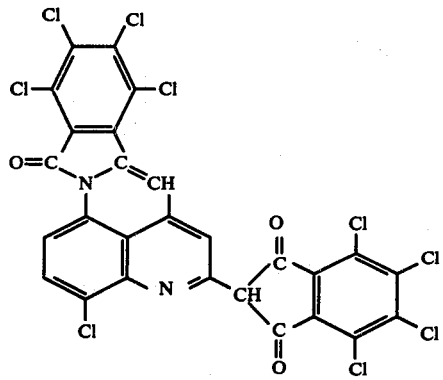

The melting point of the product was more than 360° C. Its visible absorption spectrum in a dimethyl formamide solution had a maximum value at 490 and 560 m$\mu$. In its infrared absorption spectrum, an absorption was seen at 1733 cm$^{-1}$.

The elemental analysis values as found were C; 44.95%, H: 0.62%, N: 3.68%, and Cl: 44.34%, which well agreed with the calculated values (C: 44.76%, H: 0.69%, N: 3.87%, Cl: 44.05%).

EXAMPLES E-2 to E-5

In these Examples, the procedure of Example E-1 was repeated except that the following compounds were used instead of the 8-chloro-5-amino-2,4-dimethylquinoline and tetrachlorophthalic anhydride.

Specifically, a 5-amino-2-methylquinoline of the formula

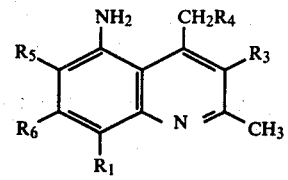

wherein $R_1$, $R_3$, $R_4$, $R_5$ and $R_6$ are as shown in Table E, was reacted in the same way as in Example E-1 with a dicarboxylic anhydride of the formula

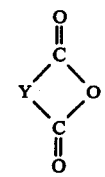

wherein Y is as shown in Table E, to afford a compound of the formula

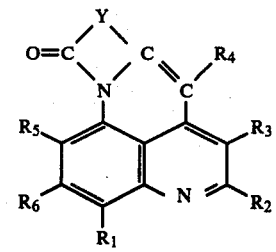

wherein $R_2$ is as shown in Table E below.

The infrared absorption spectra and the visible absorption spectra of these products are shown in Table E.

Table E

| Example | $R_1$ | $R_2$ | $R_3$ | $R_4$ | $R_5$ | $R_6$ | Y | IR characteristic absorption (cm$^{-1}$) | Absorption maximum in the visible region [$\lambda$max.(m$\mu$)] |
|---|---|---|---|---|---|---|---|---|---|
| E-2 | Cl | (phthalimide-CH) | H | H | H | H | (benzene) | 1720 | 516 484 (DMF) |
| E-3 | Cl | (tetrabromophthalimide-CH) | H | H | H | H | (tetrabromobenzene) | 1746 1721 | 574 460 (DMF) |

Table E-continued

| Example | R1 | R2 | R3 | R4 | R5 | R6 | Y | IR characteristic absorption ($cm^{-1}$) | Absorption maximum in the visible region [$\lambda max.(m\mu)$] |
|---|---|---|---|---|---|---|---|---|---|
| E-4 | $CH_3$ | (phthalimide-CH group) | $CH_3$ | H | H | H | (o-tolyl) | 1723 | 547<br>512<br>(α-CN) |
| E-5 | Cl | (phthalimide-CH group with $CO_2H$) | H | H | H | H | (p-tolyl with $CO_2H$) | 1721 | 522<br>487<br>(DMF) |

EXAMPLE F-1

68 Parts of 5-amino-8-ethyl-2,4-dimethylquinoline, 250 parts of tetrachlorophthalic anhydride and 1000 parts of α-chloronaphthalene were reacted under reflux for 4 hours. The reaction mixture was filtered at 120° C., washed twice with hot α-chloronaphthalene and then with 1500 parts of dimethyl formamide and 1500 parts of acetone to afford 175 parts of a red solid having the following structural formula:

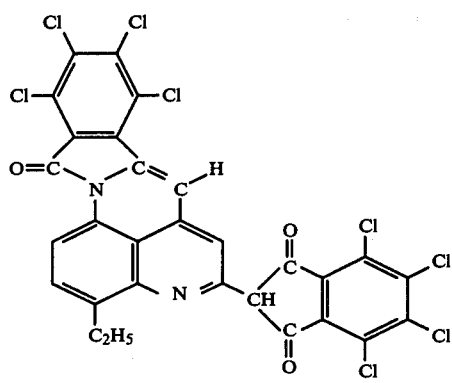

The product had a melting point of above 360° C., and the maximum values of its visible absorption spectrum in an α-chloronaphthalene solution were 520 mμ and 560 mμ. In its infrared absorption spectrum, an absorption was seen at 1720 $cm^{-1}$.

The elemental analysis values as found were C: 48.6%, H: 0.94%, N: 3.78%, and Cl: 39.46%, which well corresponded with the calculated values (C: 48.71%, H: 0.99%, N: 3.92%, Cl: 39.67%).

EXAMPLES F-2 to F-14

In these Examples, the procedure of Example F-1 was repeated except that the following compounds were used instead of the 5-amino-8-ethyl-2,4-dimethylquinoline and tetrachlorophthalic anhdride.

Specifically, a 5-amino-2-methylquinoline of the formula

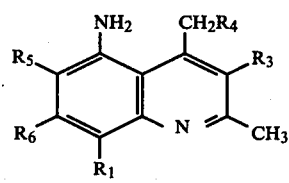

wherein $R_1$, $R_3$, $R_4$, $R_5$ and $R_6$ are as shown in Table F, was reacted in the same way as in Example F-1 with a dicarboxylic anhydride expressed by the following formula

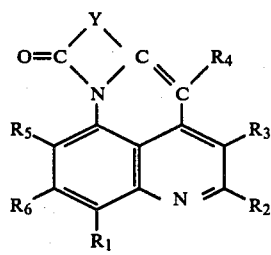

wherein Y is as shown in Table F below, to afford a compound of the following formula

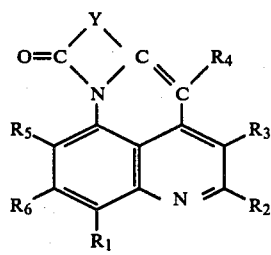

wherein $R_2$ is as shown in Table F.

The infrared absorption spectra and the visible absorption spectra of these products are shown in Table F.

Table F
| Example | R₁ | R₂ | R₃ | R₄ | R₅ | R₆ | Y | IR characteristic absorption (cm⁻¹) | Absorption maximum in the visible region [max.(mμ)] |
|---|---|---|---|---|---|---|---|---|---|
| F-2 | CH₃ | 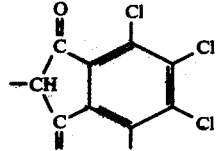 | H | H | H | H | 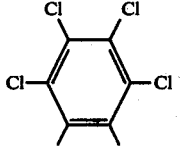 | 1721 | 550 515 (α-CN) |
| F-3 | CH₃ | 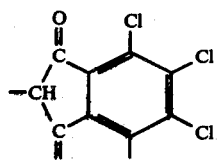 | CH₃ | H | H | H | 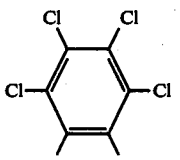 | 1729 | 515 (α-CN) |
| F-4 | CH₃ | 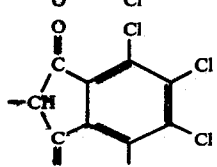 | H | H | CH₃ | H | 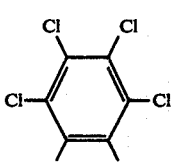 | 1729 | 502 (α-CN) |
| F-5 | H | 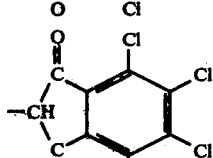 | H | H | OCH₃ | H | 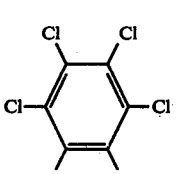 | 1742 | 460 (DMF) |
| F-6 | OCH₃ | 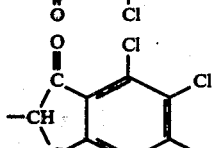 | H | H | H | H | 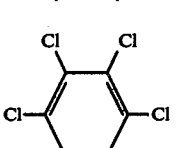 | 1745 | 540 510 (α-CN) |
| F-7 | CH₃ | 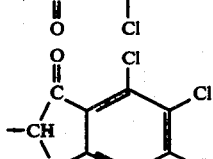 | H | CH₃ | H | H | 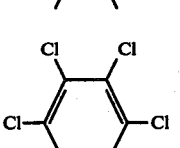 | 1740 | 560 520 (α-CN) |
| F-8 | CH₃ | 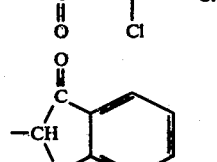 | H | CH₃ | H | H |  | 1730 | 520 488 (DMF) |
| F-9 | OCH₃ | 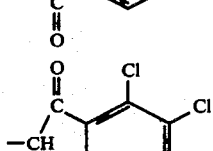 | H | CH₃ | H | H | 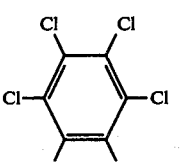 | 1740 | 550 515 (α-CN) |
| F-10 | Br | 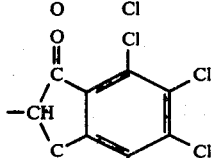 | H | CH₃ | H | H | 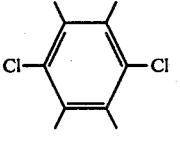 | 1735 | 552 (shoulder) 517 (α-CN) |

Table F-continued

| Example | R₁ | R₂ | R₃ | R₄ | R₅ | R₆ | Y | IR characteristic absorption (cm⁻¹) | Absorption maximum in the visible region [max.(mμ)] |
|---|---|---|---|---|---|---|---|---|---|
| F-11 | F | −CH(CO)₂C₆Cl₄ (tetrachlorophthalimidyl-methylene) | H | H | H | H | tetrachlorophenyl | 1725 | 558, 520 (α-CN) |
| F-12 | CH₃ | −CH(CO)₂C₆Br₄ (tetrabromophthalimidyl-methylene) | H | H | H | H | tetrabromophenyl | 1730 | 550, 515 (α-CN) |
| F-13 | H | −CH(CO)₂C₆Cl₄ | H | H | OH | H | tetrachlorophenyl | 1700 | 525 (α-CN) |
| F-14 | CH₃ | −CH(CO)₂C₆Cl₄ | CH₃ | CH₃ | H | H | tetrachlorophenyl | 1715 | 575 (shoulder), 525 (α-CN) |

EXAMPLE G-1

100 Parts of 5,8-diamino-2,4-dimethylquinoline, 826 parts of tetrachlorophthalic anhydride, 40 parts of zinc chloride and 2000 parts of trichlorobenzene were reacted at the boiling point under reflux for 3 hours. Then, 500 parts of dimethyl formamide was added, and the mixture was stirred under reflux for 1 hour. After cooling, the reaction mixture was filtered, and the resulting red reaction product was washed with 1000 parts of dimethyl formamide and then with ethanol, and dried to afford 440 parts of a red solid having the following structural formula:

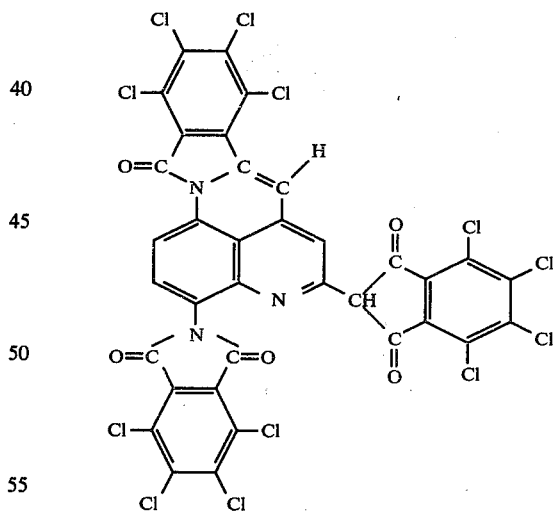

The resulting product had a melting point of more than 360° C., and the maximum absorption values of its visible absorption spectrum in a dimethyl formamide solution were 448, 530–540, and 610 mμ. In its infrared absorption spectrum, an absorption was observed at 1783 and 1730 cm⁻¹.

The elemental analysis values as found were C: 43.35%, H: 0.58%, N: 4.63% and Cl: 43.52%, which corresponded well with the calculated values (C: 43.21%, H: 0.52%, N: 4.32%, and Cl: 43.73%).

G-2

The procedure of Example G-1 was repeated except that 110 parts of 8-hydroxy-5,7-diamino-2,4-dimethylquinoline was used instead of 100 parts of 5,8-diamino-2,4-dimethylquinoline, thereby to afford 395 parts of a red solid having the following structural formula:

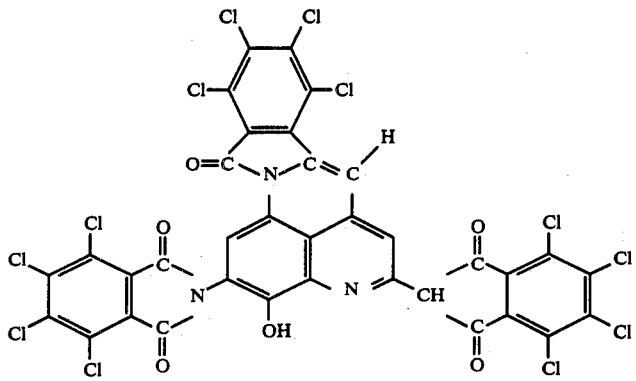

In its infrared absorption spectrum, an absorption was seen at 1780, 1740 and 1715 cm$^{-1}$. The maximum values in its visible absorption spectrum in an α-chloronaphthalene solution were 555 mμ (shoulder) and 510 mμ.

EXAMPLE H

75 Parts of 5,8-diamino-2,4-dimethylquinoline, 120 parts of 4-bromo-1,8-napthalic anhydride and 500 parts of o-xylene were heated under reflux for 1.5 hours to afford 110 parts of 8-(4'-bromonaphthalimide)-5-amino2,4-dimethylquinoline. To the product were added 176 parts of tetrachlorophthalic anhydride and 40 parts of zinc chloride. The mixture was heated under reflux for 4 hours in 2500 parts of trichlorobenzene, and then 1250 parts of dimethyl formamide was added. The mixture was heated under reflux for an additional one hour. After cooling, the reaction mixture was filtered. The resulting reddish black reaction product was washed with 1000 parts of dimethyl formamide and then with ethanol, and dried to afford 148 parts of a reddish black solid having the following structural formula:

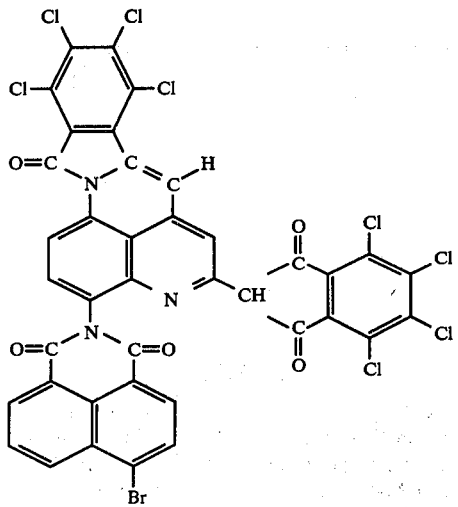

The product had a melting point of more than 360° C., and the maximum absorptions of its visible absorption spectrum in an α-chloronaphthalene solution were 522 and 599 mμ. In its infrared absorption spectrum, an absorption was seen at 1725 cm$^{-1}$.

The elemental analysis values as found were C: 49.03%, H: 1.22%, N: 4.56%, halogen: 37.02%, which well agreed with the calculated values (C: 49.22%, H: 1.03%, N: 4.31%, halogen: 37.25%).

EXAMPLE I

Ten parts of 4-(p-aminobenzyl)-5-amino-2,8-dimethylquinoline and 11 parts of phthalic anhydride were refluxed for 1 hour in 100 parts of α-chloronapthalene. Then, tetrachlorophthalic anhydride was added, and the mixture was stirred under reflux for 2.5 hours. The reaction mixture was filtered at 140° C., and washed with 100 parts of dimethyl formamide and then with acetone to attord 11 parts of a red solid having the following structural formula

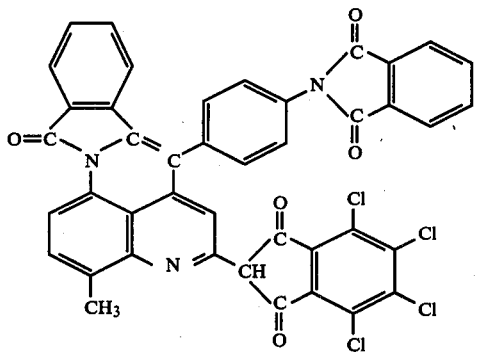

The product had a melting point of more than 360° C., and the maximum value of its visible absorption spectrum in an α-chloronaphthalene solution as 497 mμ. Its infrared absorption spectrum showed the absorption of carbonyl at 1780 and 1840 cm$^{-1}$.

EXAMPLE J-1

Ten parts of 4-(p-aminobenzyl)-5-amino-2,8-dimethylquinoline and 38 parts of tetrachlorophthalic anhydride were reacted for 2.5 hours under reflux in 100 parts of α-chloronaphthalene. The reaction mixture was hot-filtered, and washed with dimethyl formamide and then with acetone to afford 16 parts of a reddish violet solid having the following structural formula:

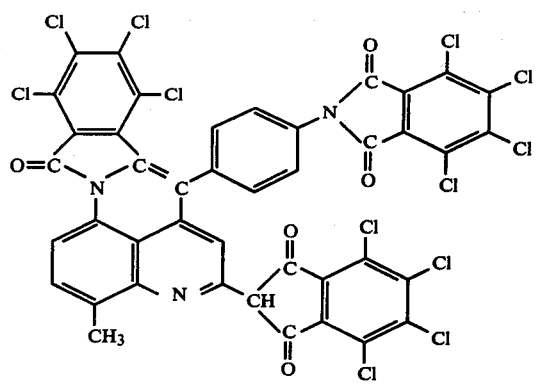

The product had a melting point of more than 360° C., and the maximum value of its visible absorption spectrum in an α-chloronapthalene solution was 522 mμ. In its infrared absorption spectrum, the absorption of carbonyl was seen at 1780 and 1723 cm⁻¹.

EXAMPLES J-2 and J-3

In these Examples, the procedure of Example J-1 was repeated except that the following compounds were used instead of the quinoline derivative and tetrachlorophthalic anhydride.

Specifically, 4-(p-aminobenzyl)-5-amino-2-methyl-quinoline derivative of the formula

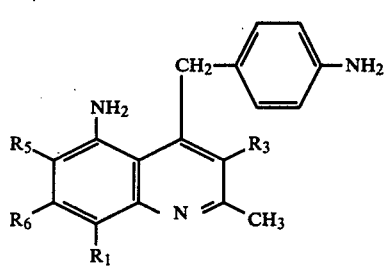

wherein $R_1$, $R_3$, $R_5$ and $R_6$ are as shown in Table G, was reacted in the same way as in Example J-1 with a dicarboxylic anhydride of the formula

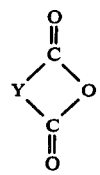

wherein Y is as shown in Table G, to afford a compound of the formula

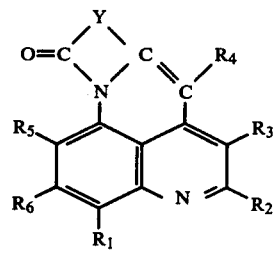

wherein $R_2$ and $R_4$ are as shown in Table G.

The infrared absorption spectra and the visible absorption spectra of the products are shown in Table G.

Table G

| Example | $R_1$ | $R_2$ | $R_3$ | $R_4$ | $R_5$ | $R_6$ | Y | IR characteristic absorption (cm⁻¹) | Absorption maximum in the visible region [λmax.(mμ)] |
|---------|-------|-------|-------|-------|-------|-------|---|---|---|
| J-2 | Cl | ![structure with -CH and two C=O groups linked to tetrachlorobenzene] | H | ![structure with p-tolyl-N and two C=O groups linked to tetrachlorobenzene] | H | H | tetrachlorobenzene | 1780, 1730 | 525 (α-CN) |
| J-3 | CH₃ | ![structure with -CH and two C=O groups linked to benzene] | H | ![structure with p-tolyl-N and two C=O groups linked to benzene] | H | H | methylbenzene | 1785, 1720 | 502 (α-CN) |

EXAMPLE K

24 Parts of the same diazaphenalene derivative as obtained in Example G and 25 parts of cyclohexylamine were reacted under reflux for 5 hours in 100 parts of dimethyl formamide. After cooling, the reaction mixture was filtered, and washed with dimethyl formamide and then with acetone to afford 14 parts of a red solid having the following structural formula:

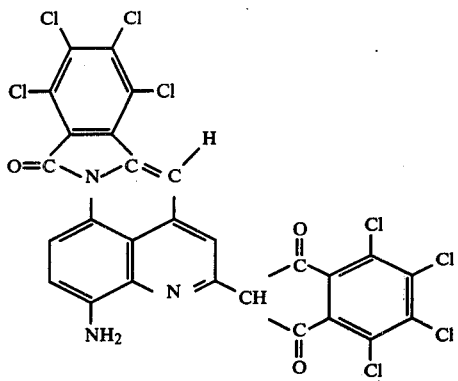

The product had a melting point of more than 360° C. The maximum wavelengths of its visible absorption spectrum in α-chloronaphthalene were 550 and 515 mμ. In its infrared absorption spectrum, the absorption of carbonyl was observed only at 1730 cm$^{-1}$.

EXAMPLE L

Twenty parts of the same diazaphenalene derivative as obtained in Example K, 9.6 parts of benzenesulfonyl-2,3-naphthalenedicarboxylic anhydride and 10 parts of zinc chloride were reacted at 240° C. for 2 hours in 200 parts of α-chloronaphthalene. After cooling, the reaction mixture was filtered, and washed with dimethyl formamide and then with acetone to afford 23 parts of a red solid. This compound had a structure which results from the imidization of the amino group of the starting diazaphenalene derivative.

The product had a melting point of more than 360° C., and the maximum wavelengths of its visible absorption spectrum in α-chloronaphthalene were 553 and 518 mμ. The absorption of carbonyl was observed at 1775 and 1730 cm$^{-1}$ in its infrared absorption spectrum.

EXAMPLE M

Twenty parts of the same diazaphenalene derivative as obtained in Example K, 3.1 parts of pyromellitic anhydride, and 10 parts of zinc chloride were reacted at 240° C. for 2 hours in 500 parts of α-chloronaphthalene. After cooling, the reaction mixture was filtered, and washed with dimethyl formamide and then with acetone to afford 13.5 parts of a reddish violet solid having the following structural formula:

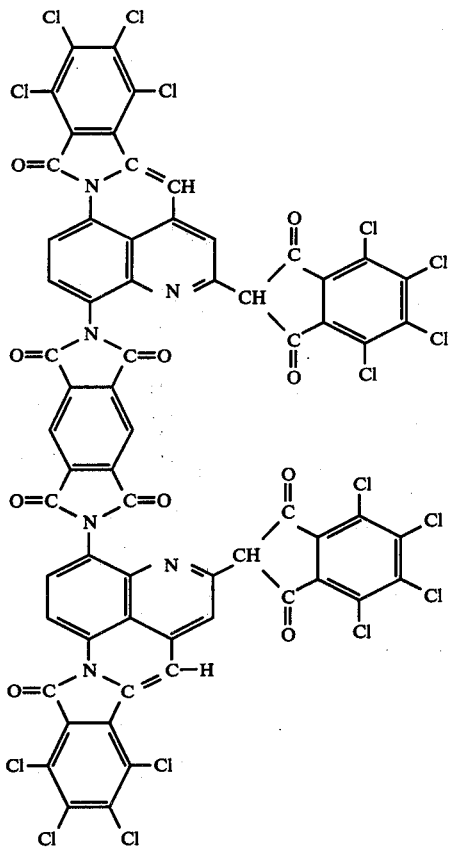

The product had a melting point of more than 360° C., and the maximum wavelengths of the visible absorption spectrum in α-chloronaphthalene were 552 and 516 mμ. In its infrared absorption spectrum, the absorption of carbonyl was observed at 1780 cm$^{-1}$.

EXAMPLE N

196 Parts of 5-amino-8-chloro-2,4-dimethylquinoline and 192 parts of trimellitic anhydride were heated for 3 hours in 1000 parts of α-chloronaphthalene. Then, 134 parts of naphthalene-1,4,5,8-tetracarboxylic anhydride was added, and the reaction was performed under heat for 4 hours. After cooling, the reaction mixture was filtered. The crystals obtained were washed with 500 parts of hot dimethyl formamide to afford 327 parts of a dark brown pigment having the following structural formula

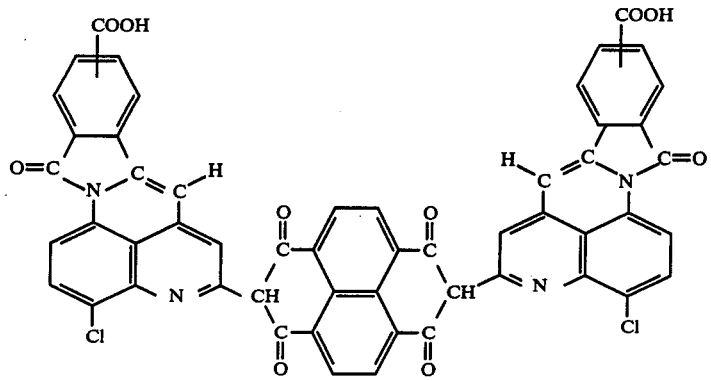

In its visible absorption spectrum in a dimethyl formamide solution, a broad absorption was seen at wavelengths of 450 to 470 mµ. In its infrared absorption spectrum, the absorption of carbonyl was observed at 1771 and 1725 cm$^{-1}$.

EXAMPLE O

200 Parts of 5-amino-8-chloro-2,4-dimethylquinoline and 110 parts of pyromellitic anhydride were heated in 1000 parts of p-xylene for 2 hours. Then, 312 parts of tetrachlorophthalic anhydride and 34 parts of zinc chloride were added, and heated under reflux for 4 hours in 500 parts of trichlorobenzene to afford 364 parts of reddish black crystals having the following structural formula:

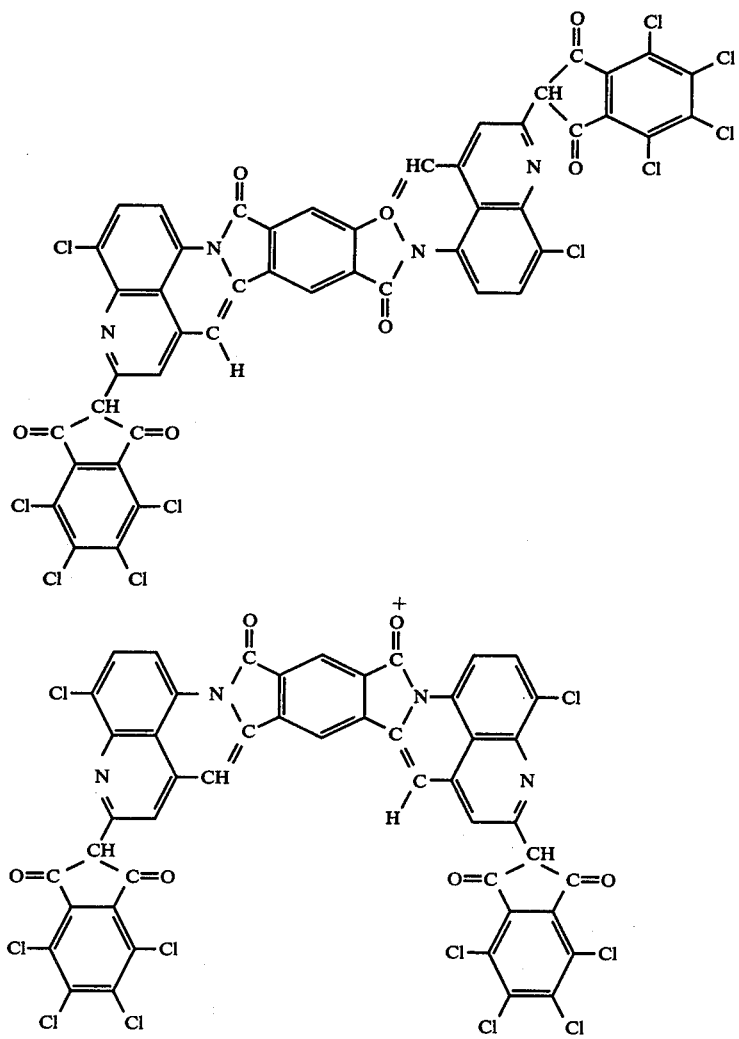

The maximum wavelengths of its visible absorption spectrum in an α-chloronaphthalene solution were 530–550 and 596 mµ, and in its infrared absorption spectrum, the absorption of carbonyl was seen at 1780 and 1720 cm$^{-1}$.

EXAMPLE P

The same procedure as in Example O was repeated except that 156 parts of benzophenone-3,4,3',4'-tetracarboxylic anhydride was used instead of the pyromellitic anhydride, thereby to afford 457 parts of deep red crystals having the following structural formula:

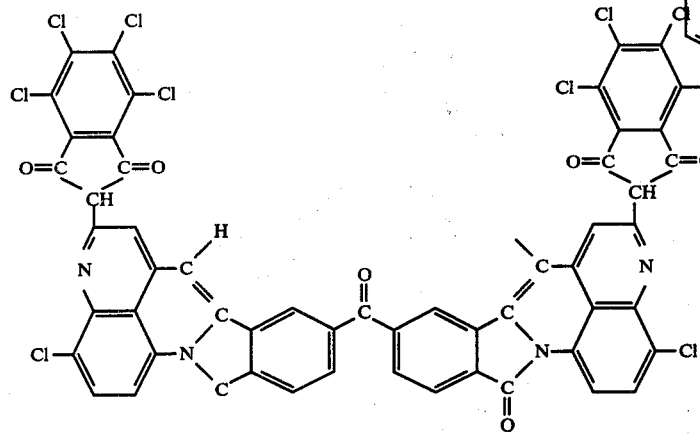

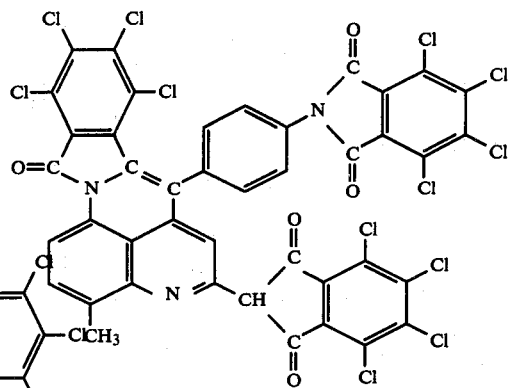

The maximum wavelengths of its visible absorption spectrum in an α-chloronaphthalene solution was 516 and 554 mμ. In its infrared absorption spectrum, an absorption was seen at 1727 cm$^{-1}$.

EXAMPLE Q

The same procedure as in Example O was repeated except that 172 parts of diphenylsulfone-3,4,3',4'-tetracarboxylic anhydride was used instead of the pyromellitic acid, thereby to afford 440 parts of deep red crystals of the following structural formula:

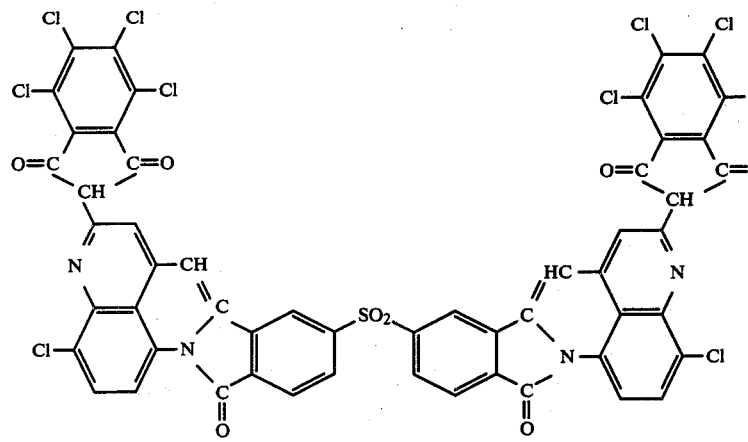

The maximum wavelengths of its visible absorption spectrum in an α-chloronaphthalene solution were 520 and 558 mμ. In its infrared absorption spectrum, an absorption was seen at 1730 cm$^{-1}$.

In the following Examples, various tests were conducted on the compounds obtained by this invention.

EXAMPLE R-1

Two parts of the compound of the following formula obtained in Example J-1 and 300 parts of di(2-ethylhexyl) phthalate were mixed with 700 parts of polyvinyl chloride, and kneaded on a two-roll mill at 155° to 160° C. to form a sheet colored red. The colored sheet was interposed between sheets of soft polyvinyl chloride, and under a load of 1 kg/cm² at 80° C. was left to stand for 24 hours. No migration of the color to the white sheet was observed, and the evaluation by a gray scale was class 5.

EXAMPLES R-2 and R-45

The same test as in Example R-1 was performed on the various compounds shown in Table H, and the results are shown in Table H. The figures in the column headed by "type of pigment" are the Example numbers.

Table H

| Example | Type of pigment | Gray scale (grade) |
|---|---|---|
| R-2 | C-3 | 5 |
| R-3 | C-4 | 5 |
| R-4 | C-5 | 5 |
| R-5 | C-8 | 5 |
| R-6 | C-9 | 5 |
| R-7 | C-10 | 5 |
| R-8 | C-11 | 5 |
| R-9 | C-12 | 5 |
| R-10 | C-13 | 5 |
| R-11 | C-14 | 5 |
| R-12 | C-15 | 5 |
| R-13 | C-16 | 5 |
| R-14 | C-17 | 5 |
| R-15 | C-18 | 5 |
| R-16 | C-19 | 5 |
| R-17 | C-20 | 5 |
| R-18 | C-21 | 5 |
| R-19 | C-22 | 5 |
| R-20 | C-23 | 5 |
| R-21 | E-1 | 5 |
| R-22 | E-3 | 5 |
| R-23 | F-1 | 5 |
| R-24 | F-2 | 5 |
| R-25 | F-3 | 5 |
| R-26 | F-4 | 5 |
| R-27 | F-5 | 5 |
| R-28 | F-6 | 5 |
| R-29 | F-7 | 5 |
| R-30 | F-9 | 5 |
| R-31 | F-10 | 5 |
| R-32 | F-11 | 5 |
| R-33 | F-12 | 5 |
| R-34 | F-13 | 5 |
| R-35 | F-14 | 5 |
| R-36 | G-1 | 5 |
| R-37 | G-2 | 5 |
| R-38 | H | 5 |
| R-39 | I | 5 |
| R-40 | J-2 | 5 |
| R-41 | M | 5 |
| R-42 | N | 5 |
| R-43 | O | 5 |
| R-44 | P | 5 |
| R-45 | Q | 5 |

EXAMPLE S-1

One part of the compound of the following structural formula which was synthesized in Example C-23,

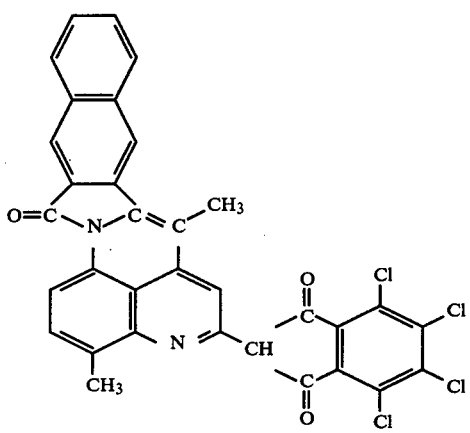

1 part of zinc stearate and 10 parts of rutile titanium oxide were mixed with 2000 parts of polyethylene, and the mixture was melt-extruded at 230° C. to form pellets colored red. The molded sheets were exposed to a weather-Ometer to perform a light resistance test. The result was rated as class 6 on a blue scale.

EXAMPLE S-2

A red pigment (1.5 parts) of the following structural formula which was synthesized in Example C-16

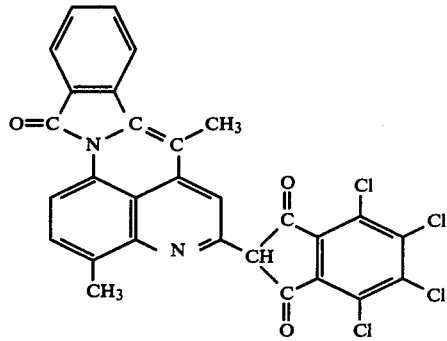

and 1.5 parts of zinc stearate were blended with 1000 parts of polyethylene, and the mixture was extruded by a melt-extruder at 220° to 230° C. to afford pellets colored red.

The pellets were injection-molded under the conditions shown in Table I to afford molded plates having brilliant deep red. The pellets showed superior thermal stability, and no difference in color was observed depending upon the differences in the injection conditions.

Table I

| Temperature of the cylinder (°C.) | Residence time (minutes) |
|---|---|
| 240 | 1 |
| 240 | 5 |
| 260 | 5 |
| 280 | 5 |
| 300 | 5 |

Examples S-3 to S-17

Each of the powdery pigments obtained in the previous Examples was mixed with the various resins shown in Table J, and the mixture was melted and injection-molded. The weatherability of the resulting specimens was measured by a carbon arc lamp test using a Weather-Ometer. The results are evaluated by a blue scale.

The thermal stability was estimated by visually observing the change of color of the specimen during its injection molding under the conditions shown in Table J.

The results are shown in Table J. The figures in the column headed "type of pigment" are the Example numbers.

Table J

| Example | Type of pigment | Amount (%) | Resin | Injection molding conditions Temp. (°C.) | Time (min.) | Thermal stability | Weatherability (class) |
|---|---|---|---|---|---|---|---|
| S-3 | C-8 | 0.15 | Polyethylene | 240–300 | 5 | No discoloration | More than 6 |
| S-4 | C-8 | 0.05 | Polyethylene (containing 0.5% TiO$_2$) | 230 | 1 | " | More than 6 |
| S-5 | C-16 | 0.05 | " | 230 | 1 | " | 6 |
| S-6 | J-1 | 0.05 | " | 230 | 1 | " | 5 |
| S-7 | I | 0.05 | " | 230 | 1 | " | 5–6 |
| S-8 | J-2 | 0.05 | " | 230 | 1 | " | 5 |
| S-9 | F-7 | 0.05 | " | 230 | 1 | " | 4–5 |
| S-10 | C-17 | 0.05 | " | 230 | 1 | " | 5–6 |
| S-11 | F-9 | 0.05 | " | 230 | 1 | " | 5–6 |
| S-12 | C-20 | 0.05 | " | 230 | 1 | " | 5–6 |
| S-13 | E-1 | 0.05 | " | 230 | 5 | " | 5 |
| S-14 | G-1 | 0.15 | Polystyrene | 230–240 | 1 | No discoloration | More than 6 |
| S-15 | Q | 0.2 | Polycarbonate | 260–280 | 1 | " | 5–6 |
| S-16 | F-2 | 0.1 | ABS (containing 0.5% TiO$_2$) | 220–280 | 2 | " | — |
| S-17 | E-3 | 0.1 | Polypropylene (containing 0.5% TiO$_2$) | 230–250 | 10–30 | " | — |

EXAMPLE T

One part of a red compound of the following structural formula

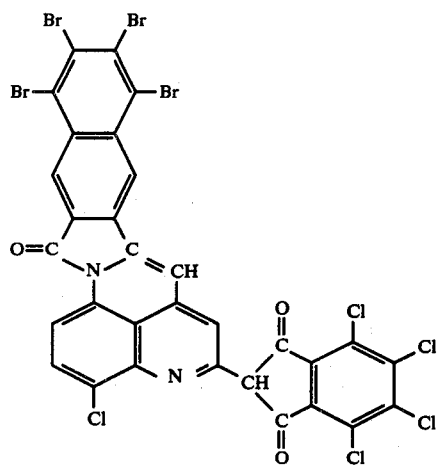

386 parts of calcium carbonate, 4 parts of zinc stearate, 25 parts of a styrene monomer, and 35 parts of finely divided polystyrene were mixed in a ball mill, and 300 parts of glass fibers, 240 parts of an isophthalic acid-derived unsaturated polyester and 10 parts of calcium hydroxide were added. A polymerization initiator was added, and the mixture was molded at 180° C. A reinforced polyester article colored brilliant red was obtained.

EXAMPLE U

18 Parts of the red compound obtained in Example E-1, 282 parts of a commercially available CLEAR (a melamine-alkyd paint) were milld in a hot mill for 40 hours. The mixture obtained was withdrawn from the pot, and thinned. The resulting coating composition was spray-coated on a tin plate. After standing for 15 minutes, the coating was baked at 130° C. for 30 minutes to afford a coated plate having a brilliant red color.

EXAMPLE V

One part of the red compound of the following structural formula

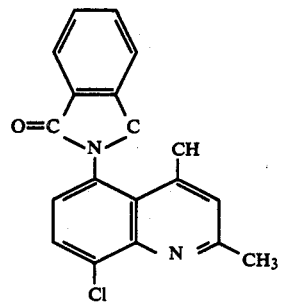

was uniformly dispersed in 3000 parts of water containing sodium higher alkyl benzenesulfonate, and 4 parts of o-phenyl phenol was added. 100 Parts of polyester fibers were dipped in the resulting dye bath and dyed at 100° to 120° C. for 2 hours. After dyeing, the fibers were washed with water, and soaped for 20 minutes at 70° C. in 3000 parts of water containing 4 parts of sulfuric acid ester of a higher alcohol to afford red dyeings.

EXAMPLE W 0.5 Part of the red pigment having the following structural formula

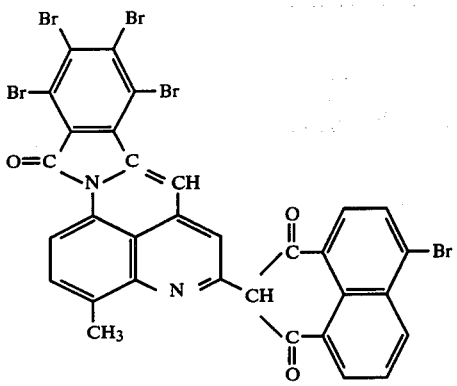

was added to 500 parts of a prepolymerized methyl methacrylate syrup. The colored syrup was poured into a glass cell, and polymerized for 6 hours at 50° to 70° C., and then for 3 hours at 100° to 130° C. It was then cooled, and removed to afford a polymethyl methacrylate resin plate having a fast red color.

EXAMPLE X

An ester-interchange reactor equipped with a rectifying column and a methanol-distilling condenser was charged with 97 parts of dimethyl terephthalate and 65 parts of ethylene glycol, and 0.088 part of calcium acetate was added as a catalyst. The mixture was heated at 140° to 230° C. while distilling off methanol formed by the reaction. In about 3 hours, the temperature of the inside of the reactor reached 235° C., and a theoretical amount of methanol was distilled off, when 0.070 part of trimethyl phosphate was added to terminate the ester-interchange reaction.

The reaction product was transferred to a polycondensation reactor equipped with a stirrer and an ethylene glycol distilling condenser. 0.044 Part of antimony trioxide and 1.5 parts of the compound of the following formula

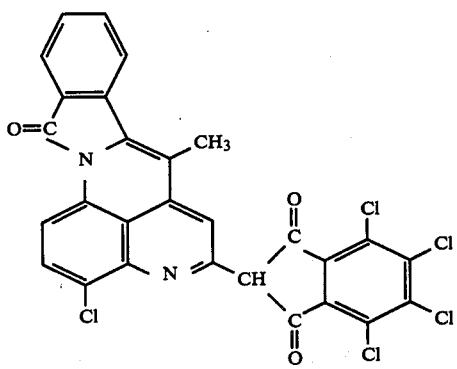

were added, and the polycondensaation was carried out for 10 minutes at 280° C. under atmospheric pressure, for 30 minutes in a vacuum of 30 to 40 mmHg, and then for 1.5 hours in a high vacuum of 0.3 mmHg. The contents were cooled, withdrawn from the reactor, and pulverized by a pulverizer. The resulting product was spun by a melt-spinning apparatus at 280° C., and drawn to form polyester filaments having a brilliant red color.

At the time of spinning and drawing, no filament breakage was observed.

EXAMPLE Y-1

100 Parts of the same compound as produced in Example C-8 and 100 parts of zinc stearate were mixed at room temperature for 1 hour in a V-type blender to form a pigment preparation. The pigment preparation had a high level of dispersibility for use in coloring polymeric materials.

EXAMPLE Y-2

100 Parts of the same compound as produced in Example C-8, 400 parts of rutile titanium oxide and 100 parts of zinc stearate were mixed at room temperature for 1 hour in a V-type blender to form a pigment preparation. The pigment preparation had a high level of dispersibility for use in coloring polymeric materials.

EXAMPLE Y-3

100 Parts of the same compound as obtained in Example C-8, 50 parts of magnesium stearate, 50 parts of tetrakis[methylene-(3,5-ditert.-butyl-4-hydroxyhydrocinnamate)] methane, and 100 parts of 2-(3', 5'-ditert.-butyl-phenyl)-S-chlorobenzotriazole were mixed at room temperature for 1 hour using a V-type blender to form a pigment preparation. This pigment prepration dispersed very well in polypropylene with little deterioration of the resin.

What we claim is:

1. A compound of the formula

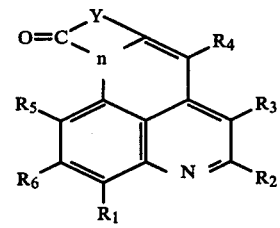

wherein $R_1$ represents a hydrogen atom, a halogen atom, a hydroxyl group, a lower alkyl group, a lower alkoxy group, a lower haloalkyl group, a phenyl or naphthyl group which is unsubstituted or monosubstituted by a lower alkyl, lower alkoxy, amide or imide group, a group of the formula

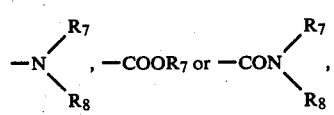

a group of the formula

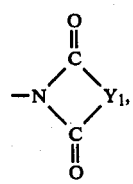

or a ground of the formula

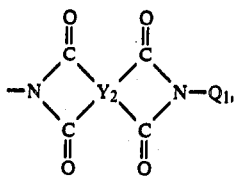

in which R₇ and R₈, independently form each other, represent a hydrogen atom, a lower alkyl group, a phenyl or naphthyl group which is unsubstituted or is monosubstituted by a lower alkyl, lower alkoxy, amide or imide group, an aryl-lower alkyl group the aryl moiety of which is a phenyl or naphthyl group and is unsubstituted or monosubstituted by a lower alkyl, lower alkoxy, amino or imide group, an acyl group of the formula R₉—CO— in which R₉ is a lower alkyl or phenyl group, or a 1,3,5-triazinyl group which is substituted by chlorophenylamino, N-methylphenylamino or the group —NH—Q₁, or R₇ and R₈ together may form a heterocyclic ring together with the nitrogen atom to which they are bonded, said heterocyclic ring being pyrrolidine, piperidine or morpholine, Y₁ represents a divalent aromatic group selected from the group consisting of:

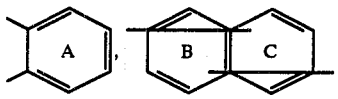

with the two bonds being present ortho or peri to each other and

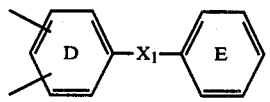

with the two bonds being present ortho to each other wherein ring A, at least one of rings B and C, and at least one of rings D and E each may have 1 to 10 substituents in total selected from the group consisting of halogen atoms, a carboxyl group, ester group of the formula —COOR₁₀ in which R₁₀ has the same meaning as group R₇ defined above, X₁ represents a direct bond or —O—,

—SO₂—, —NHCO— or a lower alkylene group, Y₂ represents a tetravalent aromatic group selected from the group consisting of:

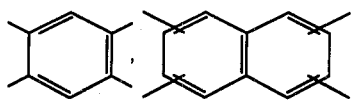

with the four bonds on the naphthalene ring forming two pairs and the two bonds in each pair being present ortho or peri to each other,

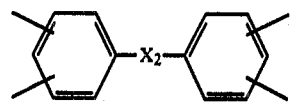

with the two bonds on each benzene ring being present ortho to each other, and

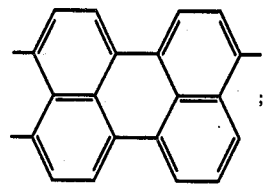

Q₁ is a monovalent group resulting from the removal of R₁ from the formula (I) above, and X₂ represents

—SO₂—, —CONH— or a lower alkylene group;
R₂ represents a hydrogen atom, a halogen atom, a lower alkyl group, a hydroxy group, a lower alkoxy group, a lower haloalkyl group, a group of the formula

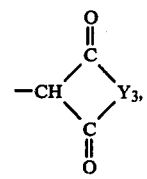

or a group of the formula

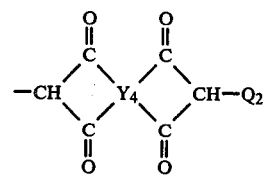

in which Y₃ is identical to or different from Y₁ and represents the same groups as does Y₁, Y₄ is identical to or different from Y₂ and represents the same groups as does Y₂, and Q₂ is a monovalent group resulting from the removal of R₂ from formula (I);
R₃, R₅ and R₆, independently from each other, represent a hydrogen atom, a halogen atom, a hydroxy group, a cyano group, a lower alkyl group, a lower alkoxy group, a lower haloalkyl group, or a group of the formula —COOR₇,

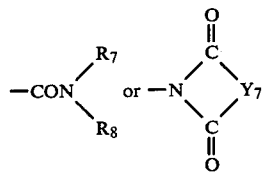

wherein $Y_7$ is identical to or different from $Y_1$ and represents the same groups as defined by $Y_1$, and $R_7$ and $R_8$ are as defined above;

$R_4$ represents a hydrogen atom, a halogen atom, a lower alkyl group, a lower alkoxy group, a lower haloalkyl group, a phenyl or naphthyl group which is unsubstituted or monosubstituted by a lower alkyl, lower alkoxy, amide or imide group, a cyano group, a group of the formula

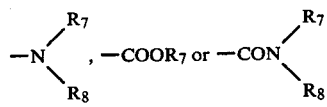

in which $R_7$ and $R_8$ are as defined above; and

Y represents a group of the formula $>Y_5$ in which $Y_5$ is identical to or different from $Y_1$ and represents the same groups as does $Y_1$, or a group of the formula $>Y_6=Q_3$ in which $Y_6$ is identical to or different from $Y_2$, and $Q_3$ is a divalent group resulting from the removal of Y from formula (I).

2. The compound of claim 1 wherein $R_1$ represents a hydrogen atom, a halogen atom, a hydroxyl group, a lower alkyl group, a lower alkoxy group, a phenyl group which is unsubstituted or monosubstituted by a lower alkyl, lower alkoxy, amide or imide group, a group of the formula

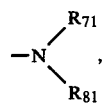

—$COOR_{71}$ or —$CONHR_{71}$, a group of the formula

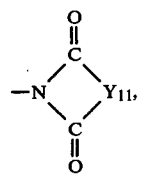

or a group of the formula

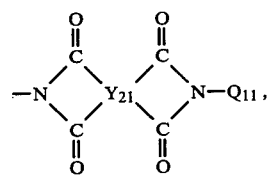

in which $R_{71}$ and $R_{81}$, independently from each other, represent a lower alkyl group, a phenyl group which is unsubstituted or is monosubstituted by a lower alkyl, lower alkoxy, amide or imide group, a pehnyl-lower alkyl group of which the phenyl moiety is unsubstituted or is mono-substituted by a lower alkyl, lower alkoxy, amide or imide group, an acyl group of the formula $R_9$—CO— in which $R_9$ is a lower alkyl or phenyl group, or a 1,3,5-triazinyl group which is substituted by chorophenylamide, N-methylphenylamino or the group —NH—Q, $Y_{11}$ represents a group of the formula the formula with the two bonds being present ortho or peri to each other, or the formula with the two bonds being present ortho to each other wherein ring A, at least one of rings B and C, and at least one of rings D and E may have up to 6 substituents intotal seclected from the group consisting of halogen atoms, a carboxyl group, lower alkoxy carbonyl groups, arylsulfonyl groups of which the aryl moiety is a phenyl or naphthyl group and is unsubstituted or is mono-substituted by a lower alkyl, lower alkoxy, amide or imide group and dicarboxylic acid anhydride groups, $X_{11}$ represents or —$SO_2$—, $Y_{21}$ represents a group of the formula the formula with the four bonds on the napthalene ring forming two pairs and the two bonds in each pair being present othero or peri to each other, or the formula with the two bonds on each benzene ring being present ortho to each other, $Q_{11}$ is a monovalent group resulting from the removal of group $R_1$ from formula (I), and $X_{21}$ represents

or $-SO_2-$.

3. The compound of claim 1 wherein $R_2$ represents a hydrogen atom, a lower alkyl group, a group of the formula

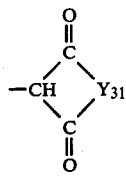

or a grup of the formula

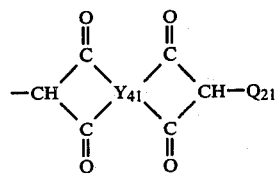

in which $Y_{31}$ is identical to or different from $Y_{11}$ and represents the same groups as does $Y_{11}$, $Y_{41}$ is identical to or different from $Y_{21}$ and represents the same groups as does $Y_{21}$ in claim 12, and $Q_{21}$ is a monovalent group resulting from the removal of group $R_2$ from formula (I).

4. The compound of claim 1 wherein $R_3$, $R_5$ and $R_6$, independently from each other, represent a hydrogen atom, a halogen atom, a hydroxyl group, a lower alkyl group, a lower alkoxy group, or a group of the formula $-NHR_{71}$, $-COOR_{71}$ or $-CONHR_{71}$ in which $R_{71}$ is a as defined in claim 2.

5. The compound of claim 1 wherein $R_4$ represents a hydrogen atom, a lower alkyl group, or a phenyl group.

6. The compound of claim 1 wherein Y is the group $Y_{51}$ which is identical to or different from $Y_{11}$, or a group of the formula $=Y_{61}=Q_{31}$ in which $Y_{61}$ represents the same groups as does $Y_{21}$ and $Q_{31}$ is a divalent group resulting from the removal of Y and wherein $Y_{11}$ represents a group of the formula

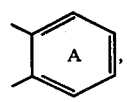

the formula

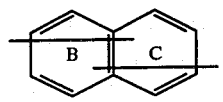

with the two bonds being present ortho or peri to each other, or the formula

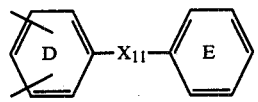

with the two bonds being present ortho to each other wherein ring A, at least one of rings B and C, and at least one of rings D and E may have up to 6 substituents in total selected from the group consisiting of halogen atoms, a carboxyl group, lower alkoxy carbonyl groups, arylsulfonyl groups of which the aryl moiety is a phenyl or naphthyl group and is unsubstituted or is mono-substituted by a lower alkyl, lower alkoxy, amide or imide group and dicarboxylic acid anhydride groups, $X_{11}$ represents

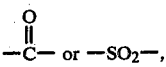

$Y_{21}$ represents a group of the formula

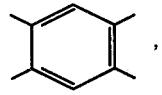

the formula

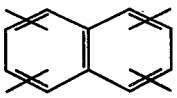

with the four bonds on the naphthalene ring forming two pairs and the two bonds in each pair being present ortho or peri to each other, or the formula

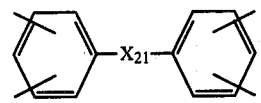

with the two bonds on each benzene ring being present ortho to each other, $Q_{11}$ is a monovalent group resulting from the removal of group $R_1$ from formula (I), and $X_{21}$ represents

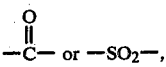

or $-SO_2-$.

7. The compound of the following formula according to claim 1

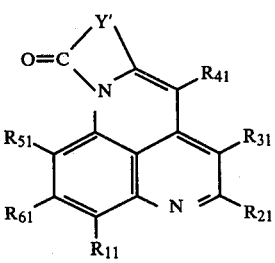

(I-a)

wherein $R_{11}$ represents a hydrogen atom, a halogen atom, a hydroxyl group, a lower alkyl group, a lower alkoxy group, or a phenyl group which is unsubstituted or is substituted by a group of the formula

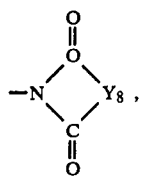

a group of the formula

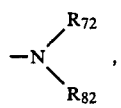

a group of the formula

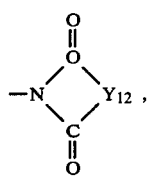

or a group of the formula

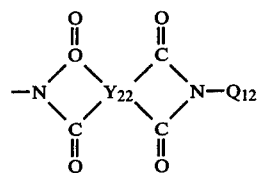

in which $R_{72}$ and $R_{82}$, independently from each other, represent a hydrogen atom, a lower alkyl group, a phenyl group, a benzyl group, an acyl group of the formula $R_{91}$—CO— in which $R_{91}$ is a lower alkyl or a phenyl group, or a 1,3,5-triazinyl group which is di-substitituted by a member selected from the group consisting of phenylamino groups and groups of the formula —NH—$Q_{12}$, $Y_{12}$ represents a divalent aromatic group selected from the group consisting of

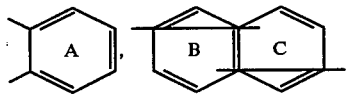

with the two bonds being present ortho or peri to each other and

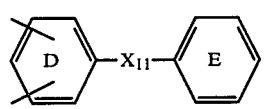

with the two bonds being present orhto to each other wherein rings A, at least one of rings B and C, and at least one of rings D and E may have up to 6 substituents selected from the group consisting of halogen atoms, a carboxyl group, lower alkoxycarbonyl groups, benzenesulfonyl groups of which phenyl group is unsubstituted or is mono-substituted by a lower alkyl, lower alkoxy, amide or imide group, and dicarboxylic acid anhydride groups, $X_{11}$ represents

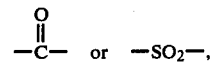

$Y_{22}$ represents a tetravelent aromatic member selected from the group consisting of

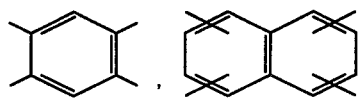

with the four bonds on the naphthalene ring forming two pairs and the two bonds in each pair being present ortho or peri to each other, and

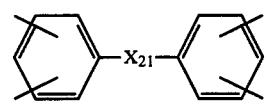

with the two bonds on each benzene ring being present ortho to each other, $Y_8$ is identical to or different from $Y_{12}$ and represents the same groups as does $Y_{12}$, $Q_{12}$ is a monovalent group resulting from the removal of $R_{11}$ from formula (I-a) and $X_{21}$ represents

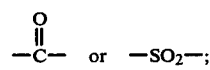

$R_{21}$ represents a hydrogen atom, a lower alkyl group, a group of the formula

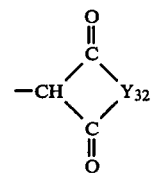

or a group of the formula

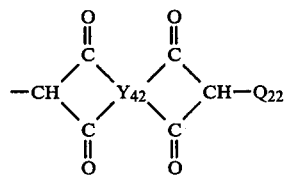

in which $Y_{32}$ is identical to or different from $Y_{12}$ and representsthe same groups as does $Y_{12}$, $Y_{42}$ is identical to or different from $Y_{22}$ and represents the same groups as does $Y_{22}$, and $Q_{22}$ is a group resulting from the removal of group $R_{21}$ from formula (I-a);

$R_{31}$, $R_{51}$ and $R_{61}$, independently from each other, represent a hydrogen atom, a halogen atom, a hydroxy group, a lower alkyl grup or a lower alkoxy group;

$R_{41}$ represents a hydrogen atom, a lower alkyl group, or a phenyl group which is unsubstituted or is substituted by

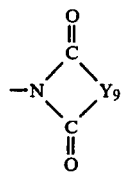

in which $Y_9$ is identical to or different from $Y_{12}$ and represents the same groups as does $Y_{12}$; and $Y'$ represents a group $Y_{52}$ which is identical to or different from $Y_{11}$ and represents the same groups as does $Y_{11}$, or a group of the formula $=Y_{62}=Q_{32}$ in which $Y_{62}$ is identical to or different from $Y_{22}$ and represents the same groups as does $Y_{22}$, and $Q_{32}$ is a divalent group resulting from the removal of $Y'$ from formula (I-a).

8. The compound of claim 7 wherein rings A, at least one of rings B and C and at least one of rings D and E have up to 4 substituents.

9. A colored composition comprising a resin and a colored compound of the general formula:

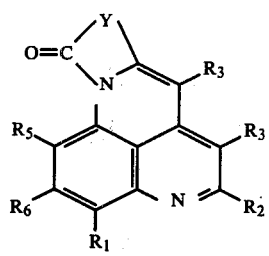 (I)

wherein $R_1$, $R_2$, $R_3$, $R_4$, $R_5$, $R_6$ and Y are as defined in claim 1.

* * * * *